(12) United States Patent
Phillips et al.

(10) Patent No.: US 11,633,497 B2
(45) Date of Patent: Apr. 25, 2023

(54) ANTI-C-MET ANTIBODY DRUG CONJUGATES

(71) Applicant: AbbVie Inc., North Chicago, IL (US)

(72) Inventors: Andrew C. Phillips, Libertyville, IL (US); Regina M. Reilly, Libertyville, IL (US); George A. Doherty, Libertyville, IL (US); Cheng Ji, Buffalo Grove, IL (US); Milan Bruncko, Green Oaks, IL (US); Erwin R. Boghaert, Pleasant Prairie, WI (US); Mark Anderson, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 17/661,450

(22) Filed: Apr. 29, 2022

(65) Prior Publication Data
US 2022/0378935 A1    Dec. 1, 2022

Related U.S. Application Data

(60) Provisional application No. 63/181,963, filed on Apr. 29, 2021.

(51) Int. Cl.
| | |
|---|---|
| A61K 47/68 | (2017.01) |
| C07K 16/28 | (2006.01) |
| A61K 39/00 | (2006.01) |
| A61P 35/00 | (2006.01) |
| C07D 491/22 | (2006.01) |
| C07K 5/068 | (2006.01) |

(52) U.S. Cl.
CPC ...... *A61K 47/6849* (2017.08); *A61K 47/6803* (2017.08); *A61P 35/00* (2018.01); *C07D 491/22* (2013.01); *C07K 5/06086* (2013.01); *C07K 16/2863* (2013.01); *A61K 2039/505* (2013.01); *C07K 2317/565* (2013.01); *C07K 2317/73* (2013.01); *C07K 2317/92* (2013.01)

(58) Field of Classification Search
CPC ............ A61K 47/6803; A61K 47/6849; A61K 2039/505; C07D 491/22; C07K 5/06086; C07K 16/2863; C07K 2317/565; C07K 2317/73; C07K 2317/92

See application file for complete search history.

(56) References Cited

U.S. PATENT DOCUMENTS

| | | | |
|---|---|---|---|
| 5,405,550 A | 4/1995 | Michl et al. | |
| 5,856,333 A | 1/1999 | Cabri et al. | |
| 6,156,754 A | 12/2000 | Lerchen et al. | |
| 6,177,439 B1 | 1/2001 | Duvvuri et al. | |
| 6,214,836 B1 | 4/2001 | Duvvuri et al. | |
| 6,350,756 B1 | 2/2002 | Yang et al. | |
| 8,329,173 B2 | 12/2012 | Goetsch | |
| 8,545,839 B2 * | 10/2013 | Goetsch ............ | C07K 16/2863 424/130.1 |
| 8,741,290 B2 | 6/2014 | Goetsch et al. | |
| 9,266,911 B2 | 2/2016 | Zhou et al. | |
| 10,344,037 B2 | 7/2019 | Li et al. | |
| 10,383,948 B2 * | 8/2019 | Allan ................ | A61K 47/6803 |
| 10,603,389 B2 | 3/2020 | Allan et al. | |
| 11,084,828 B2 | 8/2021 | Li et al. | |
| 2004/0266803 A1 | 12/2004 | Wani et al. | |
| 2005/0209263 A1 | 9/2005 | Wani et al. | |
| 2013/0109841 A1 | 5/2013 | Goetsch et al. | |
| 2016/0375042 A1 | 12/2016 | Zhou et al. | |
| 2017/0348429 A1 | 12/2017 | Reilly et al. | |
| 2018/0043033 A1 | 2/2018 | Anderl et al. | |
| 2020/0215200 A1 | 7/2020 | Allan et al. | |
| 2021/0009694 A1 | 1/2021 | Finlay | |

FOREIGN PATENT DOCUMENTS

| | | | | |
|---|---|---|---|---|
| EP | 0556585 A2 | 8/1993 | | |
| WO | 2013067449 A1 | 5/2013 | | |
| WO | 2017201204 A1 | 11/2017 | | |
| WO | 2019195665 A1 | 10/2019 | | |
| WO | WO-2019195665 A1 * | 10/2019 | ......... | A61K 31/4745 |

OTHER PUBLICATIONS

Grover, N et al. Synthetic Advances in the C H Activation of Rigid Scaffold Molecules Synthesis, vol. 52, No. 22, Nov. 2020, doi: 10.1055/s-0040-1707884, pp. 3295-3325.

* cited by examiner

*Primary Examiner* — Robert S Landsman
(74) *Attorney, Agent, or Firm* — Fox Rothschild LLP

(57) ABSTRACT

The present disclosure provides c-Met antibody drug conjugates (ADCs), including compositions and methods of using such ADCs.

Figure 1:
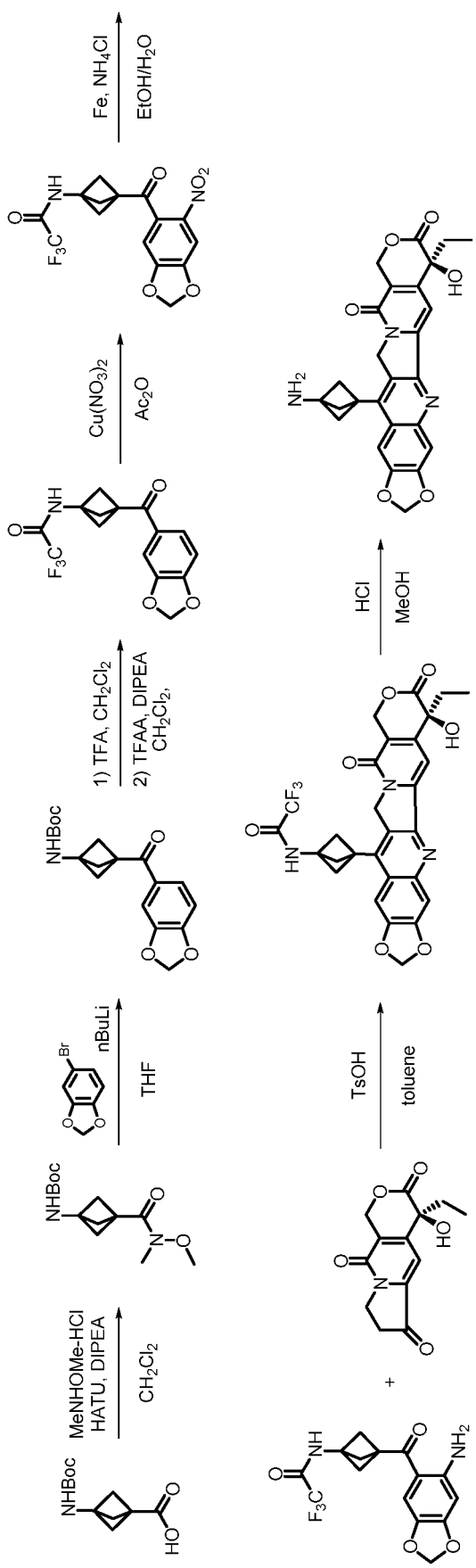

8 Claims, 9 Drawing Sheets
Specification includes a Sequence Listing.

ANTI-C-MET ANTIBODY DRUG CONJUGATES

1. CROSS REFERENCE TO RELATED APPLICATIONS

This application claims the benefit of U.S. Provisional Application Ser. No. 63/181,963, filed Apr. 29, 2021, which is hereby incorporated by reference in its entirety.

2. SEQUENCE LISTING

The instant application contains a Sequence Listing which has been submitted electronically in ASCII format and is hereby incorporated by reference in its entirety. Said ASCII copy, created on Apr. 28, 2022, is named 632US_SL_ST25.txt and is 22,918 bytes in size.

3. TECHNICAL FIELD

The present application pertains to, among other things, novel topoisomerase inhibitor drugs, drug linkers, anti-c-Met antibody drug conjugates (ADCs), and methods of making the same.

4. BACKGROUND c-Met is a signaling tyrosine kinase receptor expressed on the surface of epithelial and endothelial cells. Activation of c-Met by hepatocyte growth factor (HGF), its only known ligand, has been shown to control cell proliferation, angiogenesis, survival, and cellular motility.

Non-small cell lung cancer (NSCLC) represents 85% of all lung cancers and is the leading cause of cancer-related death worldwide. Aberrant c-Met signaling is common in NSCLC and is believed to occur via multiple mechanisms. Deregulated c-Met signaling has been associated with poor prognosis, tumorigenesis, resistance to chemotherapy/radiotherapy, and acquired resistance to epidermal growth factor receptor (EGFR) tyrosine kinase inhibitors (TKI).

Antibody drug conjugates (ADCs) represent a relatively new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen, including target surface antigens that are overexpressed or amplified in the tumor cells.

However, no antibody drug conjugates have been approved for the treatment of non-small cell lung cancer. There remains a need in the art for antibody drug conjugates that can be used for therapeutic purposes, such as in the treatment of non-small cell lung cancer.

5. SUMMARY

The present disclosure provides antibody drug conjugates that specifically bind to human c-Met. The amino acid sequences of exemplary CDRs, as well as the amino acid sequence of the $V_H$ and $V_L$ regions of the heavy and light chains of the antibody of exemplary anti-c-Met ADCs are provided in the Detailed Description below.

In another aspect, the present disclosure provides compositions including the anti-c-Met ADCs described herein. The compositions generally comprise one or more anti-c-Met ADC as described herein, and one or more excipients, carriers, or diluents.

The present disclosure provides methods of treating subjects, such as human subjects, having NSCLC comprising administering an effective amount of an anti-c-Met ADCs disclosed herein. An anti-c-Met ADC is typically administered as an intravenous infusion and/or injection.

6. BRIEF DESCRIPTION OF THE DRAWINGS

FIG. 1 shows a synthetic pathway for the topoisomerase I (TOP1) inhibitor of Formula I.

Figure 2A:
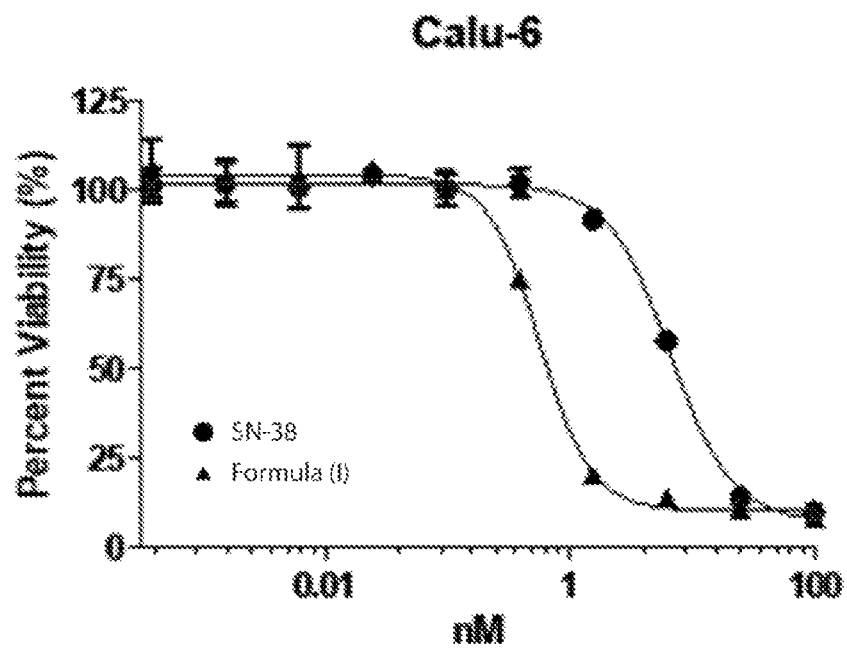
Figure 2B:
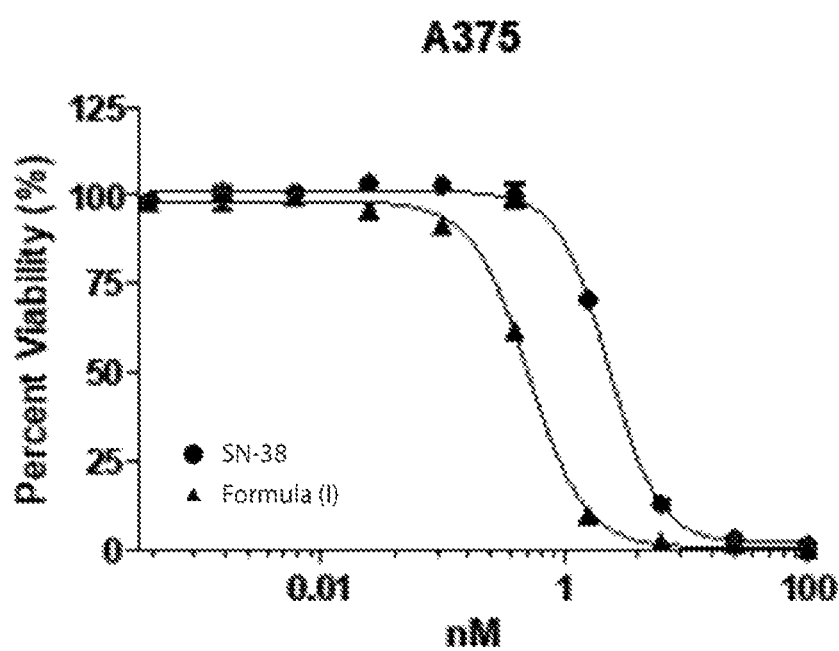
Figure 3A:
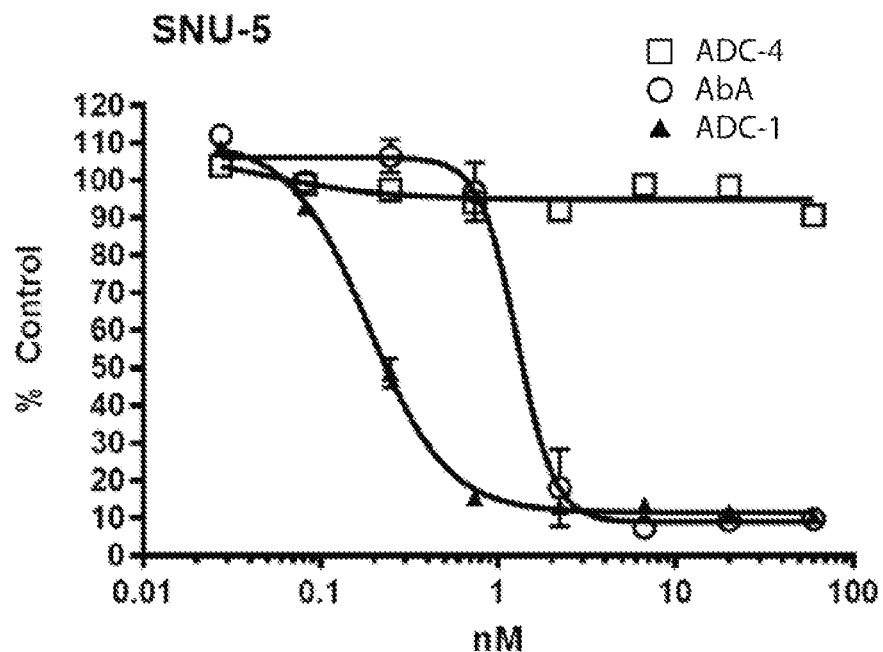
Figure 3B:
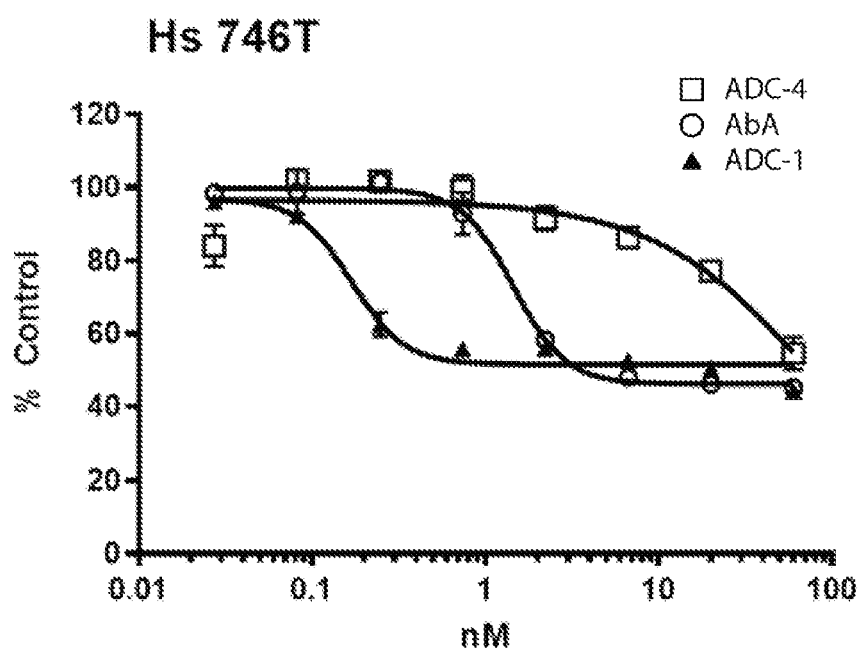
Figure 3C:
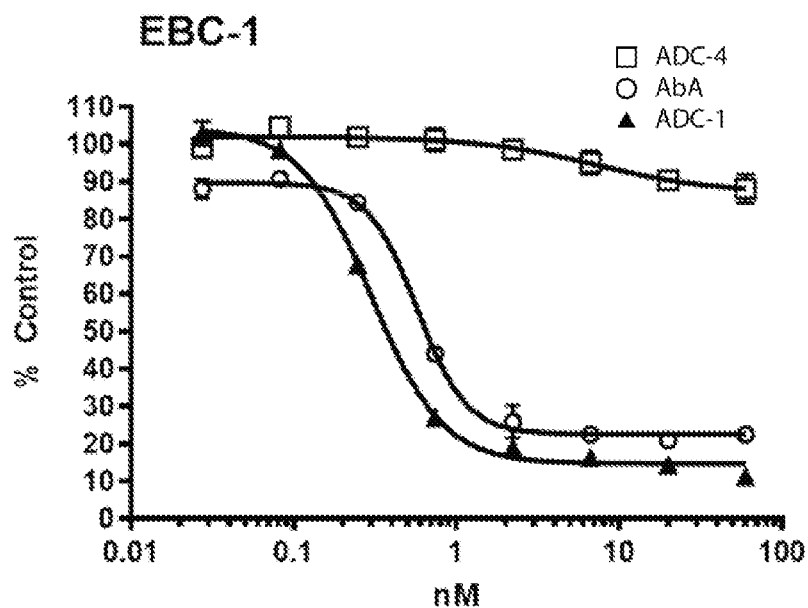
Figure 3D:
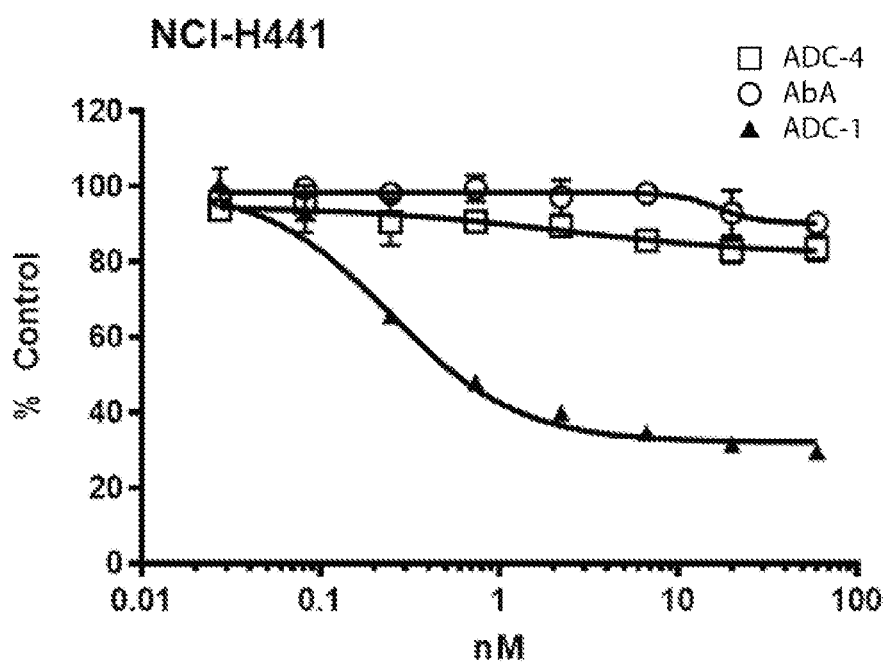
Figure 3E:
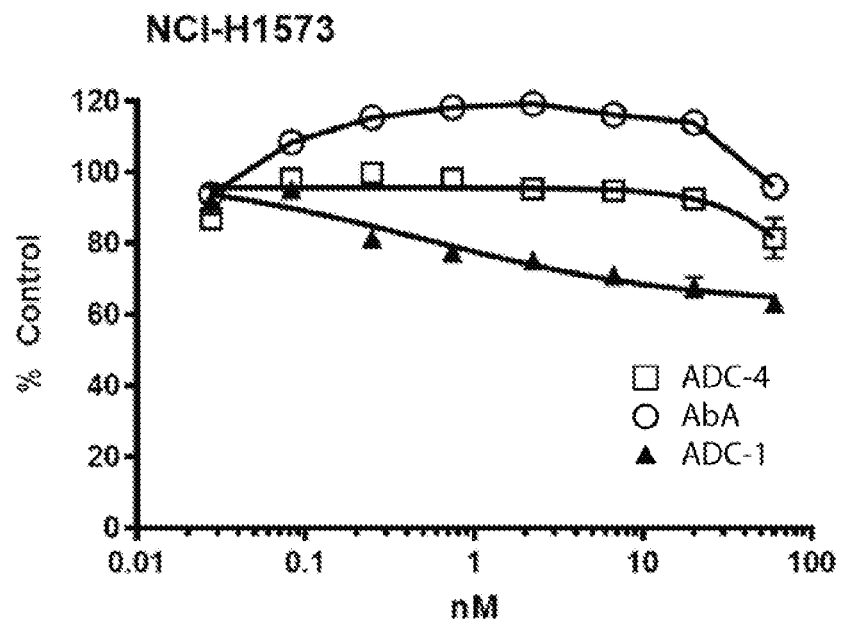
Figure 3F:
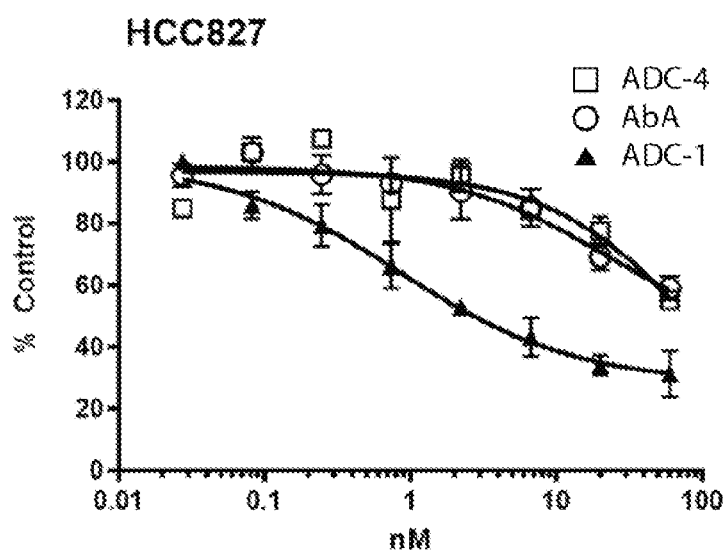
Figure 3G:
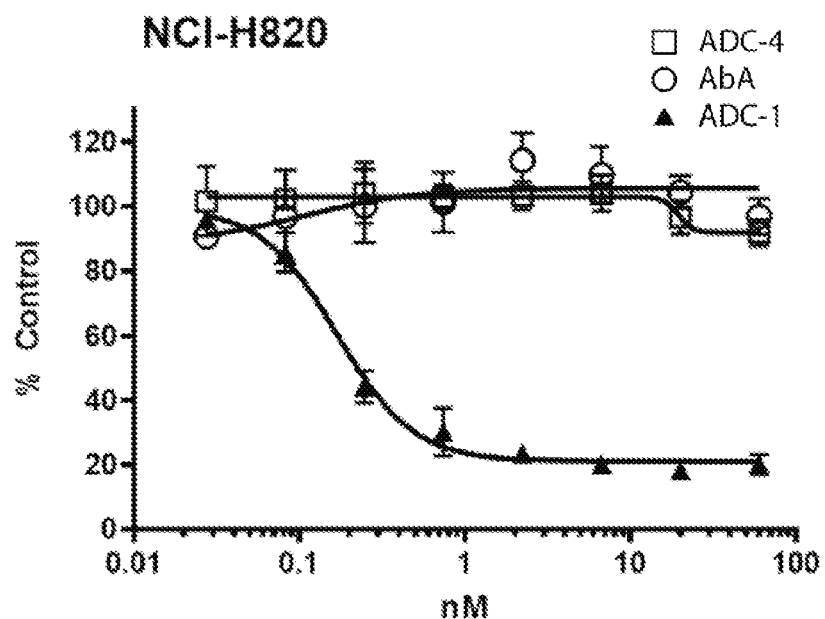
Figure 3H:
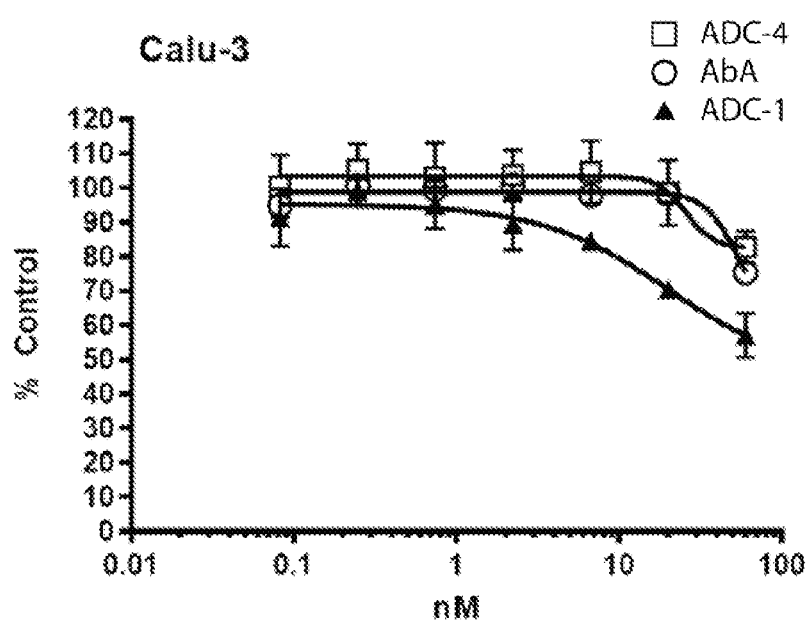
Figure 3I:
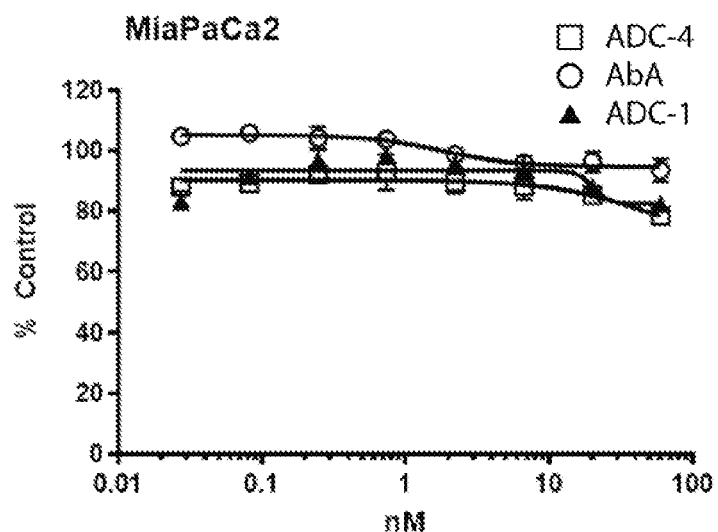
Figure 3J:
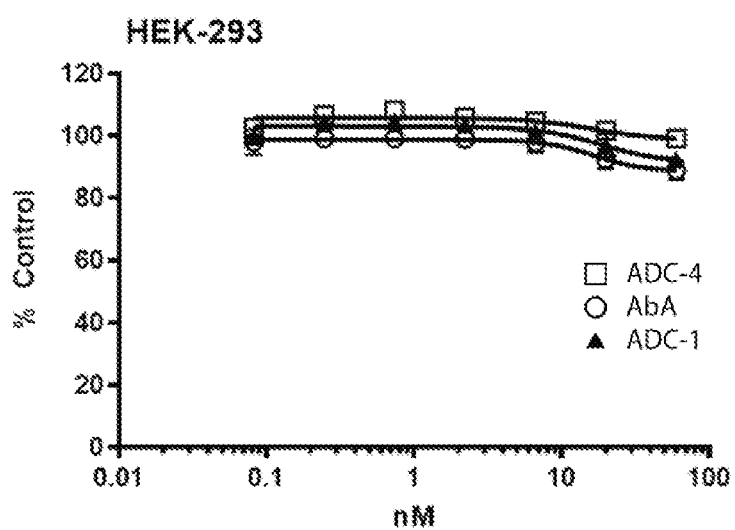

FIGS. 2A-2B show cell proliferation following administration of TOP1 inhibitor compounds for Calu-6 (lung adenocarcinoma; FIG. 2A) and A375 (malignant melanoma; FIG. 2B).

FIGS. 3A-3J show in vitro activity of an ADC of the present disclosure (ADC-1) on cell lines, including (A) SNU-5 (human gastric carcinoma), (B) Hs 746T (gastric adenocarcinoma), (C) EBC1 (human lung squamous cell carcinoma), (D) NCI-H441 (human lung adenocarcinoma), (E) NCI-H1573 (lung adenocarcinoma), (F) HCC827 (lung adenocarcinoma), (G) NCI-H820 (lung papillary adenocarcinoma), (H) Calu-3 (lung adenocarcinoma), (I) MIA PaCa-2 (pancreatic ductal adenocarcinoma), and (J) HEK-293.

Figure 4A:
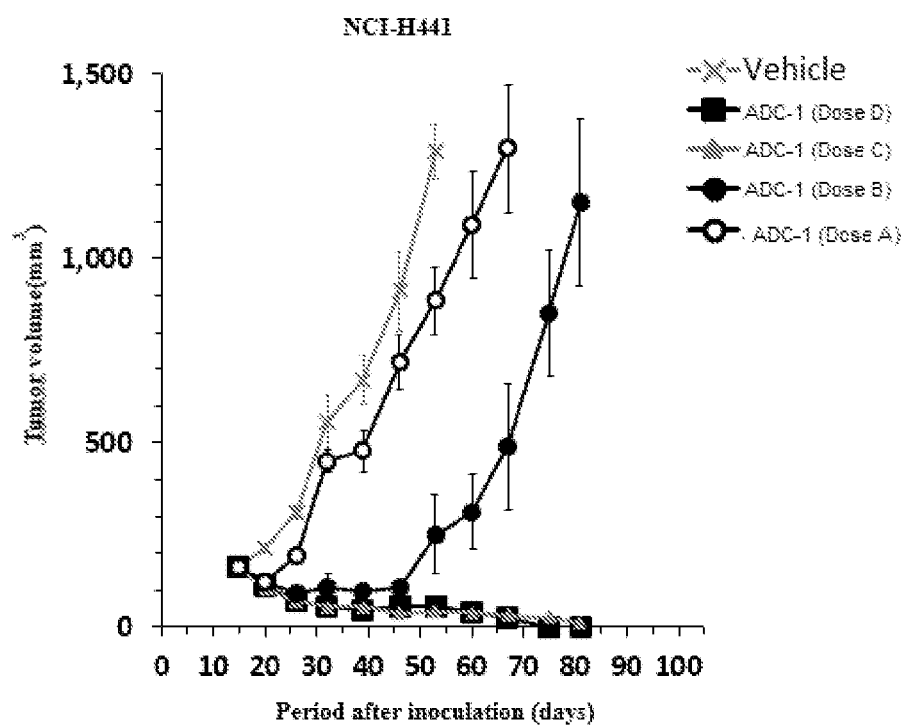
Figure 4B:
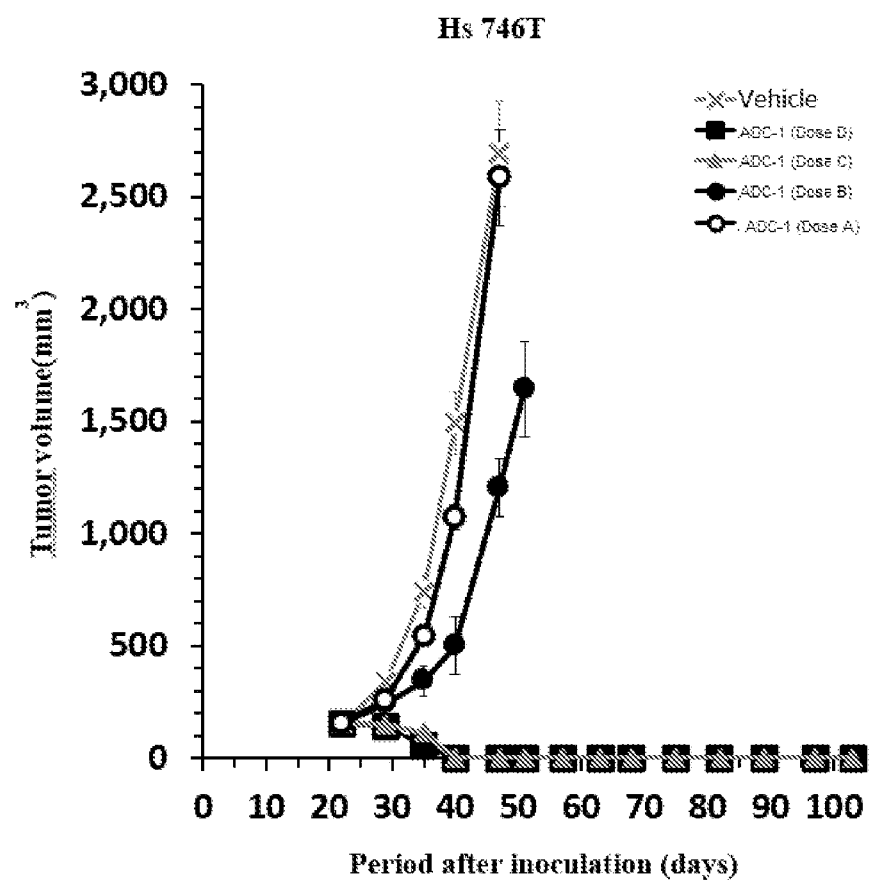

FIGS. 4A-4B show in vivo activity of ADC-1 in the NCI-H441 (human adenocarcinoma, FIG. 4A), and Hs 746T (gastric adenocarcinoma, FIG. 4B) xenograft tumor models.

7. DETAILED DESCRIPTION

Various aspects of the invention relate to topoisomerase I (TOP1) inhibitors and anti-c-Met antibody drug conjugates comprising such TOP1 inhibitors. In certain embodiments, the invention provides anti-c-Met ADCs, including anti-c-Met ADCs comprising TOP1 inhibitors, synthons useful for synthesizing the ADCs, methods of making the ADCs, and various methods of using the ADCs.

7.1. Topoisomerase 1 Inhibitors (TOP1i)

Topoisomerase 1 (TOP1) removes supercoils formed during DNA replication. TOP1 inhibitors (TOP1i) can bind and stabilize TOP1-DNA complexes, inducing DNA strand breakage and apoptosis. Presented herein is a topoisomerase I inhibitor drug ("TOP1i drug") according to structural formula (I), which may be purposed for targeted delivery to cells by conjugation to an antibody.

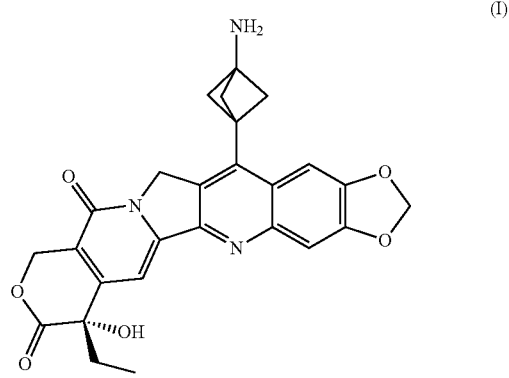 [SMILES: CC[C@@]1(O)C(=O)OCc2c1cc1n(c2=O)Cc2c-1nc1cc3c(cc1c2C12CC(N)(C1)C2)OCO3]

In embodiments, a TOP1i drug is a compound according to formula (I). In embodiments, the TOP1i drug is (7S)-14-(3-aminobicyclo[1.1.1]pentan-1-yl)-7-ethyl-7-hydroxy-2H, 10H-[1,3]dioxolo[4,5-g]pyrano[3',4': 6,7]indolizino[1,2-b]quinoline-8,11 (7H,13H)-dione , or a structurally equivalent form thereof.

TOP1i drugs as contemplated herein may be conjugated to an antibody in an ADC as shown in structural formula (II):

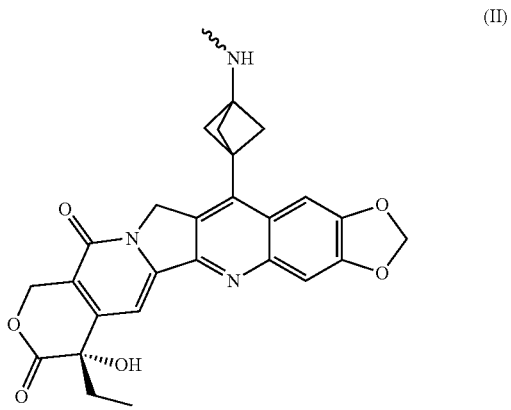

(II)

wherein $\xi$ represents the point of attachment of a linker to the TOP1i drug.

7.2. Anti-c-Met ADCs

Topoisomerase inhibitors as described herein may be conjugated to an anti-c-Met antibody to form an anti-c-Met TOP1i antibody drug conjugate (ADC). Antibody-drug conjugates may increase the therapeutic efficacy of antibodies in treating disease due to the ability of the ADC to selectively deliver one or more drug moiety(s) to target tissues, such as a tumor-associated antigen, e.g., c-Met expressing tumors. Thus, in embodiments, the present disclosure provides anti-c-Met TOP1i ADCs for therapeutic use, e.g., in the treatment of non-small cell lung cancer.

In certain embodiments, a TOP1i drug is conjugated to an antibody by way of linker according to structural formula (III):

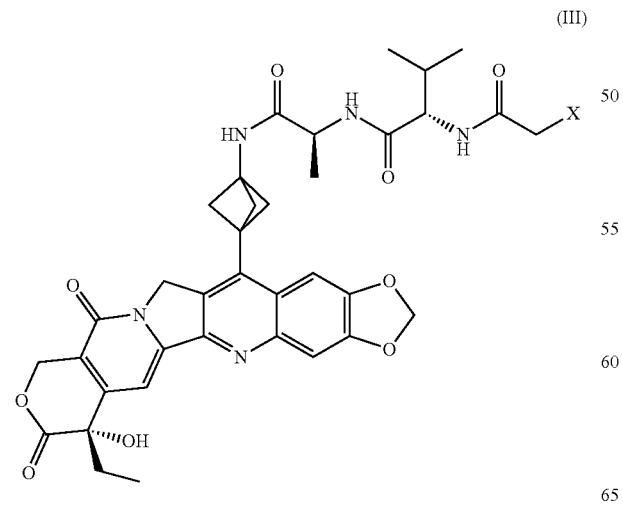

(III)

wherein X represents bromo or an N-linked maleimide.

In the anti-c-Met ADCs described herein, TOP1i drugs are conjugated to the anti-c-Met antibody by way of a linker moiety. As will be appreciated by skilled artisans, the linkers connect the TOP1i drug to the anti-c-Met antibody by forming a covalent linkage to the TOP1i drug at one location and a covalent linkage to the antibody at another. The covalent linkages are formed by reaction between functional groups on the linker and functional groups on the TOP1i drug and the anti-c-Met antibody.

Synthetic intermediate compounds that may be used to form ADCs may include:

7.2.1. Linker Drug LD1 (Structural Formula (V))

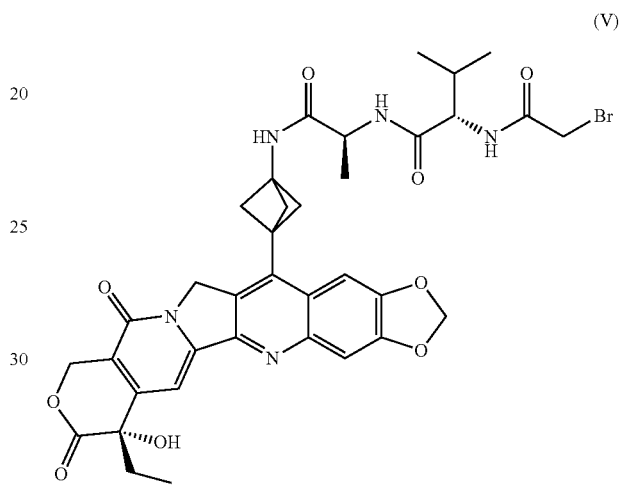

(V)

(2S)-2-(2-bromoacetamido)-N-[(2S)-1-({3-[(7S)-7-ethyl-7-hydroxy-8,11-dioxo-7,8,11,13-tetrahydro-2H,10H-[1,3]dioxolo[4,5-g]pyrano[3',4':6,7]indolizino[1,2-b]quinolin-14-yl]bicyclo[1.1.1]pentan-1-yl}amino)-1-oxopropan-2-yl]-3-methylbutanamide

7.2.2. Linker Drug LD2 (Structural Formula (VI))

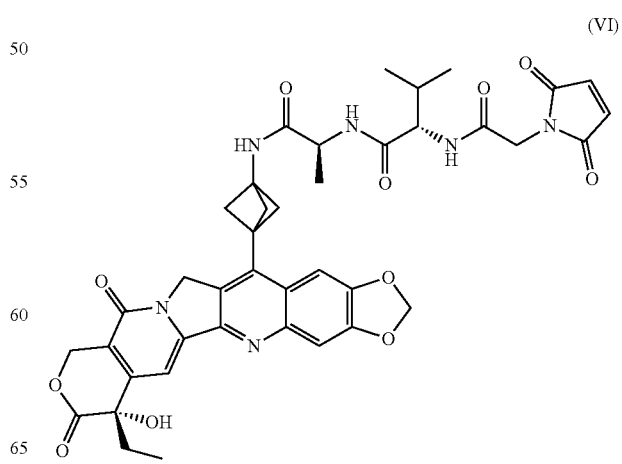

(VI)

(2S)-2-[2-(2,5-dioxo-2,5-dihydro-1H-pyrrol-1-yl)
acetamido]-N-[(2S)-1-({3-[(7S)-7-ethyl-7-hydroxy-
8,11-dioxo-7,8,11,13-tetrahydro-2H,10H-[1,3]di-
oxolo[4,5-g]pyrano[3',4':6,7]indolizino[1,2-b]
quinolin-14-yl]bicyclo[1.1.1]pentan-1-yl}amino)-1-
oxopropan-2-yl]-3-methylbutanamide

7.2.3. Linker Drug LD3 (Structural Formula (VII))

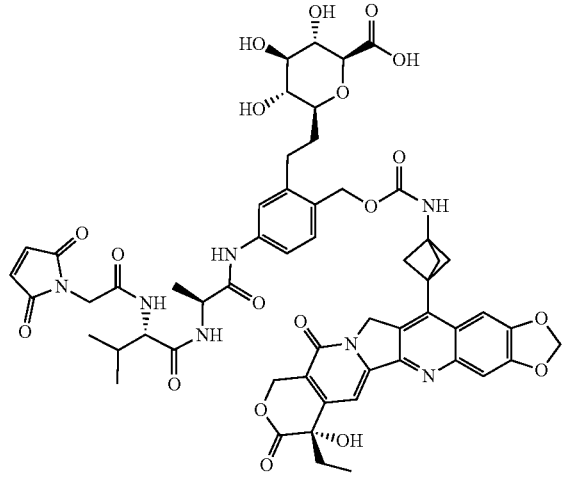

(VII)

(2S,3S,4R,5R,6S)-6-[2-(5-{[(2S)-2-({(2S)-2-[2-(2,5-
dioxo-2,5-dihydro-1H-pyrrol-1-yl)acetamido]-3-
methylbutanoyl}amino)propanoyl]amino}-2-{[{3-
[(7S)-7-ethyl-7-hydroxy-8,11-dioxo-7,8,11,13-
tetrahydro-2H,10H-[1,3]dioxolo[4,5-g]pyrano[3',4':
6,7]indolizino[1,2-b]quinolin-14-yl]bicyclo[1.1.1]
pentan-1-yl}carbamoyl)oxy]methyl}phenyl)ethyl]-
3,4,5-trihydroxyoxane-2-carboxylic acid

7.2.4. Number of Linked Drugs

The ADCs disclosed herein comprise drug molecules linked to antibody moieties in various stoichiometric molar ratios depending on the configuration of the antibody and, at least in part, the method used to effect conjugation.

The terms "drug load" or "drug loading" refer to the number of drug molecules per antibody in an individual ADC molecule. The number of TOP1i drugs linked to an anti-c-Met ADC can vary and will be limited by the number of available attachments sites on the anti-c-Met antibody. As contemplated for the anti-c-Met ADCs of the invention, the linker will link a single TOP1i drug to the antibody an anti-c-Met ADC. As long as the anti-c-Met ADC does not exhibit unacceptable levels of aggregation under the conditions of use and/or storage, anti-c-Met ADCs (i.e., structural formula (III)) having an n of up to 10 are contemplated. In some embodiments, the anti-c-Met ADCs have an n of in the range of from 1-10. In some embodiments, the anti-c-Met ADCs have an n selected from 1, 2, 3, 4, 5, 6, 7, 8, 9, or 10. In embodiments, n is 2, 4, 6, 8, or 10. In embodiments, n is 6. In embodiments, the drug loading may comprise 1 drug molecule, 2 drug molecules, 3 drug molecules, 4 drug molecules, 5 drug molecules, 6 drug molecules, 7 drug molecules, 8 drug molecules, 9 drug molecules, or 10 drug molecules.

7.2.5. Antibody AbA

AbA is a humanized version of mouse monoclonal antibody 224G11, which was first disclosed and embodied in U.S. Patent No. 8,329,173. The murine antibody m224G11 has a variable heavy domain set forth as SEQ ID NO: 13 and a variable light domain set forth as SEQ ID NO: 14:

m224G11 Heavy Chain Variable Domain (CDRs underlined, and set forth as SEQ ID NOs: 15, 16, and 17)

```
                                              (SEQ ID NO: 13)
EVQLQQSGPELVKPGASVKISCKTSGYIFTAYTMHWVRQ

SLGESLDWIGGIKPNNGLANYNQKFKGKATLTVDKSSST

AYMDLRSLTSEDSAVYYCARSEITTEFDYWGQGTALTVSS
``` m224G11 Light Chain Variable Domain (CDRs underlined, and set forth as SEQ ID NOs: 18, 19, and 20):

```
                                              (SEQ ID NO: 14)
DIVLTQSPASLAVSLGQRATISCRASESVDSYANSFMHWYQ

QKPGQPPKLLIYRASNLESGIPARFSGSGSRTDFTLTINPV

EADDVATYYCQQSKEDPLTFGSGTKLEMK
```

AbA is a humanized recombinant IgG1$_\kappa$ (disclosed as 224G11 [TH7 Hz3] in U.S. Pat. No. 8,741,290) that targets a unique epitope of c-Met located within the immunoglobulin-plexin-transcription factor homology (IPT) domain 1, resulting in blockade of both HGF-dependent and HGF-independent c-Met signaling.

As defined under the IMGT nomenclature, the CDR sequences of AbA comprise the following sequences:

| | |
|---|---|
| CDR-H1:<br>GYIFTAYT | (SEQ ID NO: 1) |
| CDR-H2:<br>IKPNNGLA | (SEQ ID NO: 2) |
| CDR-H3:<br>ARSEITTEFDY | (SEQ ID NO: 3) |
| CDR-L1:<br>ESVDSYANSF | (SEQ ID NO: 4) |
| CDR-L2:<br>RAS | (SEQ ID NO: 5) |
| CDR-L3:<br>QQSKEDPLT | (SEQ ID NO: 6) |

In some embodiments, the anti-c-Met antibodies composing an ADC of this disclosure comprise a CDR-H1 having the amino acid sequence shown as SEQ ID NO: 1, a CDR-H2 having the amino acid sequence shown as SEQ ID NO: 2; a CDR-H3 having the amino acid sequence shown as SEQ ID NO: 3, a CDR-L1 having the amino acid sequence shown as SEQ ID NO: 4, a CDR-L2 having the amino acid sequence shown as SEQ ID NO: 5; and a CDR-L3 having the amino acid sequence shown as SEQ ID NO: 6.

In some embodiments, the anti-c-Met antibodies composing an ADC of this disclosure comprise a heavy chain variable region comprising the amino acid sequence shown as SEQ ID NO: 7:

(SEQ ID NO: 7)
QVQLVQSGAEVKKPGASVKVSCKASGYIFTAYTMHWVRQ

APGQGLEWMGWIKPNNGLANYAQKFQGRVTMTRDTSIST

AYMELSRLRSDDTAVYYCARSEITTEFDYWGQGTLVTVS

S;

and a light chain variable region comprising the amino acid sequence shown as SEQ ID NO: 8:

(SEQ ID NO: 8)
DIVMTQSPDSLAVSLGERATINCKSSESVDSYANSFLHW

YQQKPGQPPKLLIYRASTRESGVPDRFSGSGSGTDFTLT

ISSLQAEDVAVYYCQQSKEDPLTFGGGTKVEIK.

In some embodiments, the anti-c-Met antibodies composing an ADC of this disclosure comprise a heavy chain comprising the amino acid sequence shown as SEQ ID NO: 9 (constant regions are bold; CDRs are underlined (disclosed as SEQ ID NOS: 1-3, respectively, in order of appearance)):

QVQLVQSGAE VKKPGASVKV SCKAS<u>GYIFT</u> <u>AYT</u>MHWVRQA PGQGLEWMGW 050

<u>IKPNNGLANY</u> AQKFQGRVTM TRDTSISTAY MELSRLRSDD TAVYYCA<u>RSE</u> 100

<u>ITTEFDY</u>WGQ GTLVTVSSAS TKGPSVFPLA PSSKSTSGGT AALGCLVKDY 150

FPEPVTVSWN SGALTSGVHT FPAVLQSSGL YSLSSVVTVP SSSLGTQTYI 200

CNVNHKPSNT KVDKRVEPKS CDCHCPPCPA PELLGGPSVF LFPPKPKDTL 250

MISRTPEVTC VVVDVSHEDP EVKFNWYVDG VEVHNAKTKP REEQYNSTYR 300

VVSVLTVLHQ DWLNGKEYKC KVSNKALPAP IEKTISKAKG QPREPQVYTL 350

PPSREEMTKN QVSLTCLVKG FYPSDIAVEW ESNGQPENNY KTTPPVLDSD 400

GSFFLYSKLT VDKSRWQQGN VFSCSVMHEA LHNHYTQKSL SLSPG 445
(full-length sequence disclosed as SEQ ID NO: 9)

and a light chain comprising the amino acid sequence shown as SEQ ID NO: 10 (CDR sequences disclosed as SEQ ID NOS: 4-6, respectively, in order of appearance):

DIVMTQSPDS LAVSLGERAT INCKS<u>SESVD SYANSFL</u>HWY QQKPGQPPKL 050

LIY<u>RASTRES</u> GVPDRFSGSG SGTDFTLTIS SLQAEDVAVY YC<u>QQSKEDPL</u> 100

<u>T</u>FGGGTKVEI KRTVAAPSVF IFPPSDEQLK SGTASVVCLL NNFYPREAKV 150

QWKVDNALQS GNSQESVTEQ DSKDSTYSLS STLTLSKADY EKHKVYACEV 200

THQGLSSPVT KSFNRGEC 218
(full-length sequence disclosed as SEQ ID NO: 10).

In embodiments, an antibody of the present disclosure comprises a heavy chain of SEQ ID NO: 9 and a light chain of SEQ ID NO: 10.

In one embodiment, the heavy chain of an anti-c-Met antibody composing an ADC of this disclosure is encoded by the following nucleotide sequence (full-length sequence disclosed as SEQ ID NO: 21):

(SEQ ID NO: 21)
ATGGGATGGTCTTGGATCTTTCTGCTGTTTCTGTCT

GGTACTGCTGGTGTGCTGAGCcaggtccagctggt gcaatccggcgcagaggtgaagaagccaggcgctt ccgtgaaggtgagctgtaaggcctct<u>ggctacatc</u>

<u>ttcacagcatacacc</u>atgcactgggtgaggcaagc tcctgggcagggactggagtggatgggatg<u>gatta</u>

<u>aacccaacaatgggctggcc</u>aactacgcccagaaa ttccagggtagggtcactatgacaagggataccag catcagcaccgcatatatggagctgagcaggctga ggtctgacgacactgctgtctattattgc<u>gccagg</u>

<u>agcgaaattacaacagaattcgattact</u>gggggca gggcaccctggtgaccgtgtcctctgccagcacca agggcccaagcgtgttccccctggcccccagcagc aagagcaccagcggcggcacagccgccctgggctg cctggtgaaggactacttccccgagcccgtgaccg tgtcctggaacagcggagccctcacttctggagtt catacct tcccagcagtattgcagagcagtggcct gtattcactgtcttccgtcgtaacagttccatcct ccagcctcgggacacagacttacatttgtaacgtg aatcacaagcctagcaacaccaaggtcgacaagag agttgaaccaaagagttgtgattgccactgtcctc cctgcccagctcctgagctgcttggcggtcccagt gtcttcttgtttccccctaaacccaaagacaccct gatgatctcaaggactcccgaggtgacatgcgtgg tggtggatgtgtctcatgaggacccagaggtgaag ttcaactggtacgtggacggcgtggaggtgcacaa cgccaagaccaagcccagagaggagcagtacaaca gcacctacagggtggtgtccgtgctgaccgtgctg caccaggactggctgaacggcaaggagtacaagtg taaggtgtccaacaaggccctgccagccccaatcg aaaagaccatcagcaaggccaagggccagccaaga gagccccaggtgtacaccctgccacccagcaggga ggagatgaccaagaaccaggtgtccctgacctgtc tggtgaagggcttctacccaagcgacatcgccgtg gagtgggagagcaacggccagcccgagaacaacta caagaccaccccccagtgctggacagcgacggca gcttcttcctgtacagcaagctgaccgtggacaag agcagatggcagcagggcaacgtgttcagctgctc cgtgatgcacgaggccctgcacaaccactacaccc agaagagcctgagcctgtccccaggctga Secretion signal peptide in bold CAPITAL letters; includes final stop codon (TGA); constant region is bold; CDRs are underlined (CDR sequences disclosed as SEQ ID NOS: 22-24, respectively, in order of appearance)

In one embodiment, the light chain of an anti-c-Met antibody composing an ADC of this disclosure is encoded by the following nucleotide sequence (full-length sequence disclosed as SEQ ID NO: 25):

(SEQ ID NO: 25)
ATGGAAACTGATACACTGCTGCTGTGGGTCCTGCTGC

TGTGGGTCCCTGGAAGCACAGGGgacattgtgatgac ccagtctcccgatagcctggccgtgtccctgggcgag agggctaccatcaactgtaaaagctcc<u>gaatctgtgg</u>

<u>actcttacgcaaacagcttt</u>ctgcactggtatcagca aaagccaggccaacctccaaagctgctgatttac<u>agg</u>

<u>gcttct</u>accagggagagcggcgtgcccgataggttca gcggatctggcagcggcaccgactttacactgaccat ctccagcctgcaggccgaagatgtggcagtctattac tgc<u>cagcagtccaaggaggaccccctgac</u>tttcgggg gtggtactaaagtggagatcaagc<u>gtacggtggccgc</u> tcccagcgtgttcatcttccccccaagcgacgagcag ctgaagagcggcaccgccagcgtggtgtgtctgctga caacttctacccagggaggccaaggtgcagtggaa ggtggacaacgccctgcagagcggcaacagccaggag agcgtcaccgagcaggacagcaaggactccacctaca gcctgagcagcaccctgaccctgagcaaggccgacta cgagaagcacaaggtgtacgcctgtgaggtgacccac cagggcctgtccagccccgtgaccaagagcttcaaca ggggcgagtgctga Secretion signal peptide in bold CAPITAL letters; includes final stop codon (TGA); constant region is bold; CDRs are underlined (CDR sequences disclosed as SEQ ID NOS: 26-28, respectively, in order of appearance).

7.2.6. Exemplary Anti-c-Met ADCs

In particular embodiments, anti-c-Met ADCs of the invention comprise an anti-c-Met antibody comprising six complementarity determining regions (CDRs) corresponding to the CDRs of antibody AbA, which is conjugated to a TOP1i drug through a cleavable valine alanine (va) linker. In certain embodiments, the linker comprises a bromoacetamide functional group for conjugation to a sulfhydryl of a reduced cysteine from the anti-c-Met antibody of the ADC. In other embodiments, the linker comprises a maleimide functional group for conjugation to a sulfhydryl of a reduced cysteine from the anti-c-Met antibody of the ADC. In some embodiments, the linker further comprises a self-immolating spacer, preferably p-aminobenzylcarbonyl (PABC) or an analogue thereof.

In embodiments, an anti-c-Met ADC comprises an anti-c-Met antibody comprising six complementarity determining regions (CDRs) corresponding to the CDRs of antibody AbA, which is conjugated to linker drug LD1 (structural formula (V)) via a linkage formed with a sulfhydryl group of a cysteine residue of the anti-c-Met antibody. In some embodiments, the anti-c-Met antibody comprises the variable heavy (VH) chain and variable light (VL) chain region sequences of antibody AbA. In some embodiments, the anti-c-Met antibody comprises the heavy chain (HC) and light chain (LC) sequences of antibody AbA.

In embodiments, an anti-c-Met ADC has the following structural formula (VIII):

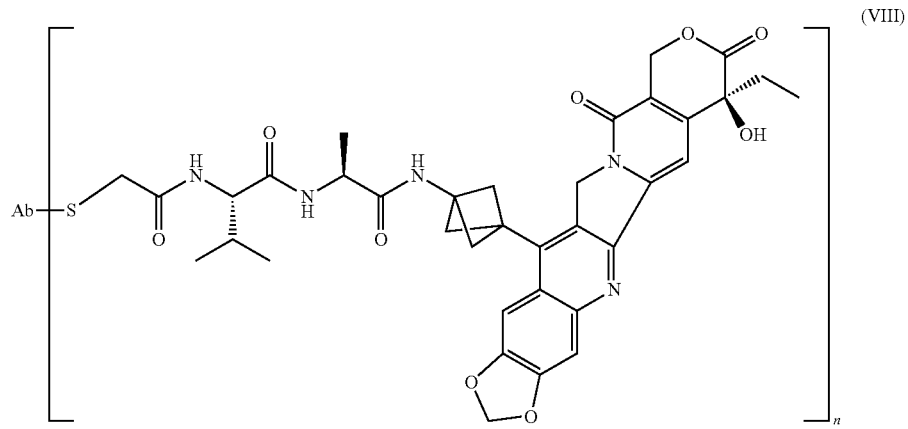

(VIII)

wherein n is an integer from 1-10, and wherein Ab is an IgG1 anti-c-Met antibody comprising a heavy chain CDR1 shown as SEQ ID NO: 1, a heavy chain CDR2 shown as SEQ ID NO: 2, a heavy chain CDR3 shown as SEQ ID NO: 3, a light chain CDR1 shown as SEQ ID NO: 4, a light chain CDR2 shown as SEQ ID NO: 5, and a light chain CDR3 shown as SEQ ID NO: 6. In embodiments, the antibody Ab is an IgG1 anti-c-Met antibody comprising a heavy chain variable region comprising the amino acid sequence shown as SEQ ID NO: 7 and a light chain variable region comprising the amino acid sequence shown as SEQ ID NO: 8. In embodiments, the antibody Ab is an anti-c-Met antibody comprising a heavy chain comprising the amino acid sequence shown as SEQ ID NO: 9 and a light chain comprising the amino acid sequence shown as SEQ ID NO: 10. In embodiments, conjugation of the linker-drug to the antibody is via a linkage formed with a sulfhydryl group of a cysteine residue of the antibody. In embodiments, n has a value of 1, 2, 3, 4, 5, 6, 7, 8, 9, or 10. In embodiments, n has a value of 2, 4, 6, 8, or 10. In embodiments, n is 6. In an embodiment, anti-c-Met ADC of structural formula (VIII) comprises an antibody Ab having a heavy chain comprising the amino acid sequence shown as SEQ ID NO: 9 and a light chain comprising the amino acid sequence shown as SEQ ID NO: 10 and n has a value of 2, 4, 6, 8, or 10. In an embodiment, anti-c-Met ADC of structural formula (VIII) comprises an antibody Ab having a heavy chain comprising the amino acid sequence shown as SEQ ID NO: 9 and a light chain comprising the amino acid sequence shown as SEQ ID NO: 10 and n has a value of 6.

In certain embodiments, an anti-c-Met ADC comprises an anti-c-Met antibody comprising six complementarity determining regions (CDRs) corresponding to the CDRs of antibody AbA, which is conjugated to linker drug LD2 (structural formula (VI)) via a linkage formed with a sulfhydryl group of a cysteine residue of the anti-c-Met antibody. In some embodiments, the anti-c-Met antibody comprises the variable heavy (VH) chain and variable light (VL) chain region sequences of antibody AbA. In some embodiments, the anti-c-Met antibody comprises the heavy chain (HC) and light chain (LC) sequences of antibody AbA.

In some embodiments, an anti-c-Met ADC has the following structural formula (IX):

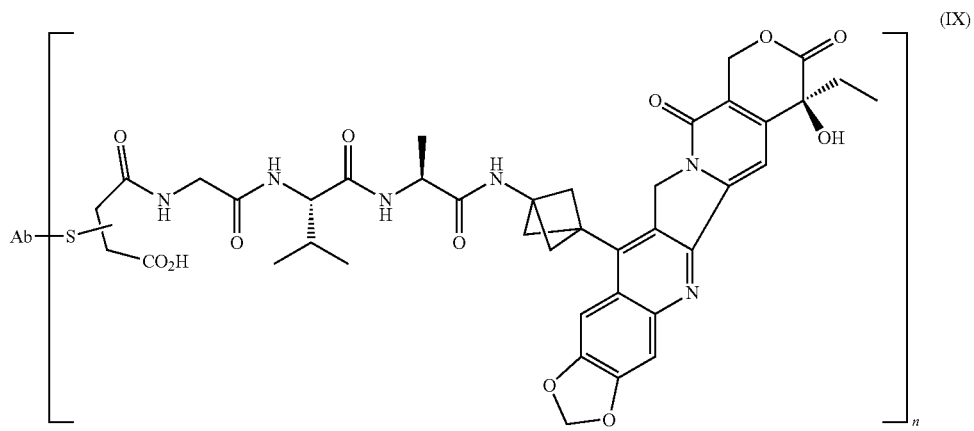

(IX)

wherein n is an integer from 1-10, and wherein Ab is an IgG$_1$ anti-c-Met antibody comprising a heavy chain CDR1 shown as SEQ ID NO: 1, a heavy chain CDR2 shown as SEQ ID NO: 2, a heavy chain CDR3 shown as SEQ ID NO: 3, a light chain CDR1 shown as SEQ ID NO: 4, a light chain CDR2 shown as SEQ ID NO: 5, and a light chain CDR3 shown as SEQ ID NO: 6. In embodiments, the antibody Ab is an IgG1 anti-c-Met antibody comprising a heavy chain variable region comprising the amino acid sequence shown as SEQ ID NO: 7 and a light chain variable region comprising the amino acid sequence shown as SEQ ID NO: 8. In embodiments, the antibody Ab is an anti-c-Met antibody comprising a heavy chain comprising the amino acid sequence shown as SEQ ID NO: 9 and a light chain comprising the amino acid sequence shown as SEQ ID NO: 10. In embodiments, conjugation of the linker-drug to the antibody is via a linkage formed with a sulfhydryl group of a cysteine residue of the antibody. In embodiments, n has a value of 1, 2, 3, 4, 5, 6, 7, 8, 9, or 10. In embodiments, n has a value of 2, 4, 6, 8, or 10. In embodiments, n is 6. In an embodiment, anti-c-Met ADC of structural formula (IX) comprises an antibody Ab having a heavy chain comprising the amino acid sequence shown as SEQ ID NO: 9 and a light chain comprising the amino acid sequence shown as SEQ ID NO: 10, and n has a value of 2, 4, 6, 8, or 10. In an embodiment, anti-c-Met ADC of structural formula (IX) comprises an antibody Ab having a heavy chain comprising the amino acid sequence shown as SEQ ID NO: 9 and a light chain comprising the amino acid sequence shown as SEQ ID NO: 10 and n has a value of 6.

In certain embodiments, an anti-c-Met ADC comprises an anti-c-Met antibody comprising six complementarity determining regions (CDRs) corresponding to the CDRs of antibody AbA, which is conjugated to linker drug LD3 (structural formula (VII)) via a linkage formed with a sulfhydryl group of a cysteine residue of the anti-c-Met antibody. In some embodiments, the anti-c-Met antibody comprises the variable heavy (VH) chain and variable light (VL) chain region sequences of antibody AbA. In some embodiments, the anti-c-Met antibody comprises the heavy chain (HC) and light chain (LC) sequences of antibody AbA.

In some embodiments, an anti-c-Met ADC has the following structural formula (X):

variable region comprising the amino acid sequence shown as SEQ ID NO: 7 and a light chain variable region comprising the amino acid sequence shown as SEQ ID NO: 8. In embodiments, the antibody Ab is an anti-c-Met antibody comprising a heavy chain comprising the amino acid sequence shown as SEQ ID NO: 9 and a light chain comprising the amino acid sequence shown as SEQ ID NO: 10. In embodiments, conjugation of the linker-drug to the antibody is via a linkage formed with a sulfhydryl group of a cystine residue of the antibody. In embodiments, n has a value of 1, 2, 3, 4, 5, 6, 7, 8, 9, or 10. In embodiments, n has a value of 2, 4, 6, 8, or 10. In embodiments, n is 6. In an embodiment, anti-c-Met ADC of structural formula (X) comprises an antibody Ab having a heavy chain comprising the amino acid sequence shown as SEQ ID NO: 9 and a light chain comprising the amino acid sequence shown as SEQ ID NO: 10 and n has a value of 2, 4, 6, 8, or 10. In an embodiment, anti-c-Met ADC of structural formula (X) comprises an antibody Ab having a heavy chain comprising the amino acid sequence shown as SEQ ID NO: 9 and a light chain comprising the amino acid sequence shown as SEQ ID NO: 10 and n has a value of 6.

The ADCs of this disclosure may be provided as a composition suitable for administration to a subject. In some embodiments, the ADC composition is a pharmaceutical composition, comprising an ADC of this disclosure and a pharmaceutically acceptable carrier. A given formulation of the ADCs disclosed herein may comprise a distribution of antibodies having differing drug loading, i.e., differing values of n.

7.3. Methods of Use

In embodiments, the methods described herein involve treating patients who have non-squamous NSCLC with the anti-c-Met ADCs of the invention.

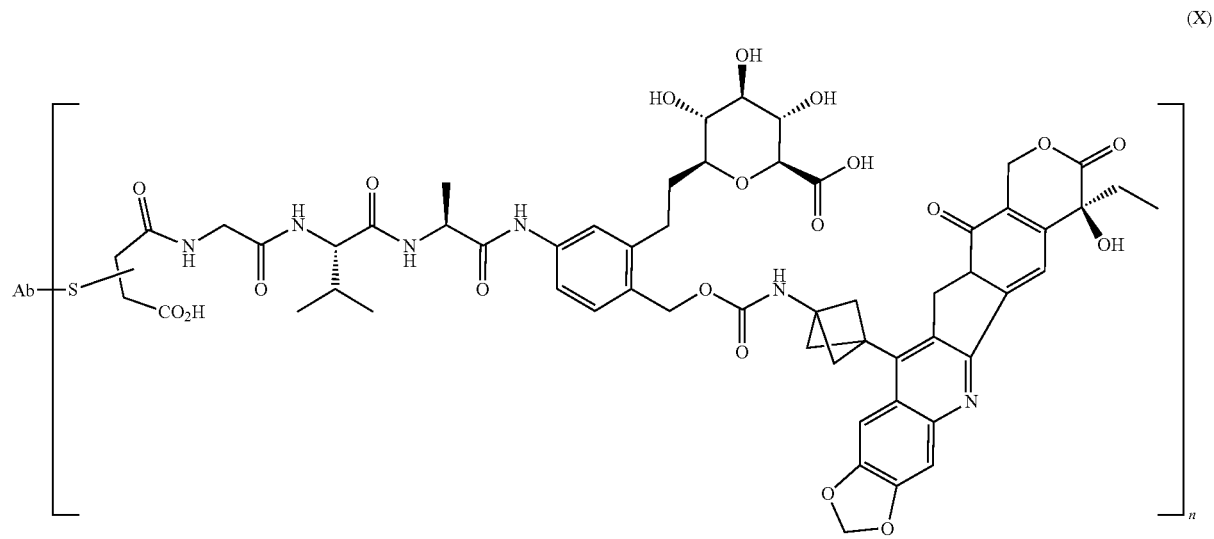

(X)

wherein n is an integer from 1-10, and wherein Ab is an IgG$_1$ anti-c-Met antibody comprising a heavy chain CDR1 shown as SEQ ID NO: 1, a heavy chain CDR2 shown as SEQ ID NO: 2, a heavy chain CDR3 shown as SEQ ID NO: 3, a light chain CDR1 shown as SEQ ID NO: 4, a light chain CDR2 shown as SEQ ID NO: 5, and a light chain CDR3 shown as SEQ ID NO: 6. In embodiments, the antibody Ab is an IgG$_1$ anti-c-Met antibody comprising a heavy chain

8. EXAMPLES

The following Examples, which highlight certain features and properties of the exemplary embodiments of the antibodies and binding fragments described herein are provided for purposes of illustration.

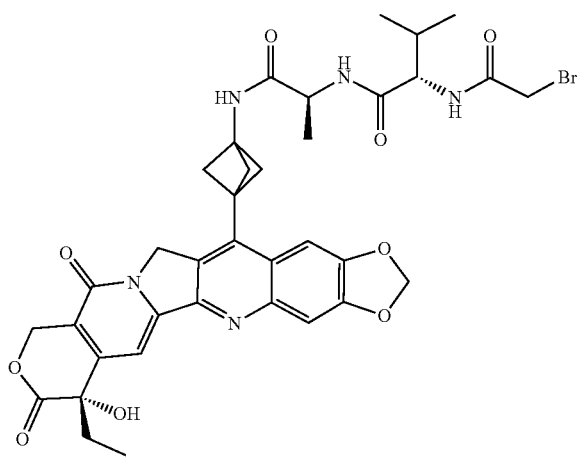 [SMILES: CC[C@@]1(O)C(=O)OCc2c1cc1n(c2=O)Cc2c-1nc1cc3c(cc1c2C12CC(NC(=O)[C@H](C)NC(=O)[C@@H](NC(=O)CBr)C(C)C)(C1)C2)OCO3]

Example 1

(2S)-2-(2-bromoacetamido)-N-[(2S)-1-({3-[(7S)-7-ethyl-7-hydroxy-8, 11-dioxo-7,8,11,13-tetrahydro-2H,10H-[1,3]dioxolo[4,5-g]pyrano[3',4':6,7]indolizino[1,2-b]quinolin-14-yl]bicyclo[1.1.1]pentan-1-yl}amino)-1-oxopropan-2-yl]-3-methylbutanamide

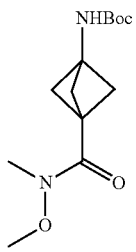 [SMILES: CON(C)C(=O)C12CC(NC(=O)OC(C)(C)C)(C1)C2]

Example 1A tert-butyl (3-(methoxy(methyl)carbamoyl)bicyclo[1.1.1]pentan-1-yl)carbamate To a solution of 3-((tert-butoxycarbonyl)amino)bicyclo[1.1.1]pentane-1-carboxylic acid (4.9 g), N,O-dimethylhydroxylamine hydrochloride (2.2 g) and N,N-diisopropylethylamine (11.30 mL) in dichloromethane (10 mL) was added 14bis(dimethylamino)methylene1-1H-1,2,3-triazolo[4,5-b]pyridinium 3-oxide hexafluorophosphate (8.61 g) in portions at 10° C. The reaction mixture was stirred at 20° C. for 12 hours. Two additional reactions were set up and allowed to stir at 20° C. for 12 hours as described. All three reactions were combined. The reaction was diluted with dichloromethane (200 mL) and added to I N aqueous HCl (50 mL). The precipitate formed was filtered and the filtrate was allowed to separate. The organic layer was washed with saturated aqueous sodium bicarbonate solution (50 mL) and brine (50 mL), dried over anhydrous sodium sulfate, filtered, and concentrated under reduced pressure. The residue was purified by chromatography on silica gel, eluting with 1-50% ethyl acetate in petroleum ether to give the title compound. $^1$H NMR (400 MHz, CDCl$_3$) δ ppm 4.97 (br s, 1H), 3.66 (s, 3H), 3.18 (s, 3H), 2.34 (s, 6H), 1.45 (s, 9H). MS (ESI+) m/z 271.2 (M+H)$^+$.

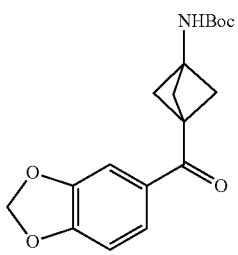 [SMILES: CC(C)(C)OC(=O)NC12CC(C(=O)c3ccc4c(c3)OCO4)(C1)C2]

Example 1B tert-butyl (3-(benzo[d][1,3]dioxole-5-carbonyl)bicyclo[1.1.1]pentan-1-yl)carbamate To a solution of 5-bromobenzo [d][1,3]dioxole (8.83 g) in tetrahydrofuran (100 mL) was added n-butyllithium (17.57 mL, 2.5 M in hexane) slowly at -65° C. under nitrogen gas. The mixture was stirred at −65° C. for 30 minutes. A solution of Example 1A (4.75 g) in tetrahydrofuran (40 mL) was added slowly. The mixture was stirred at −65° C. for 3 hours. Three additional reactions were set up and allowed to stir at −65° C. for 3 hours. All four reactions were combined. The mixture was quenched with saturated aqueous ammonium chloride solution (500 mL) and extracted with ethyl acetate (3×500 mL). The combined organic layers were washed with brine (500 mL), dried over anhydrous sodium sulfate, filtered, and concentrated under reduced pressure. The residue was purified by chromatography on silica gel, eluting with 1-50% ethyl acetate in petroleum ether to give the title compound. $^1$H NMR (400 MHz, CDCl$_3$) δ ppm 7.63 (dd, 1H), 7.45 (d, 1H), 6.82 (d, 1H), 6.03 (s, 2H), 5.04 (br s, 1H), 2.50 (s, 6H), 1.46 (s, 9H). MS (ESI+) m/z 354.2 (M+Na)$^+$.

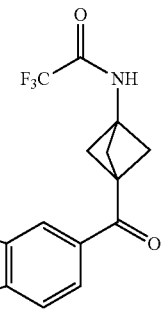

Example 1C

N-(3-(benzo [d][1,3]dioxole-5-carbonyl)bicyclo[1.1.1]pentan-1-yl)-2,2,2-trifluoroacetamide Step 1: To a solution of Example 1B (6.2 g) in dichloromethane (62 mL) was added trifluoroacetic acid (62 mL) slowly at 0° C. The reaction was stirred at 25° C. for 4 hours. Two additional reactions were set up and stirred at 25° C. for 4 hours. Each mixture was concentrated under reduced pressure. Each residue was used in the next step without further purification.

Step 2: To a solution of crude product above in dichloromethane (62 mL) was added N,N-diisopropylethylamine (16.34 mL) and trifluoroacetic anhydride (3.96 mL) drop-

17 wise at 0° C. The mixture was stirred at 25° C. for 2 hours. Two additional reactions were set up as described and stirred at 25° C. for 2 hours. All three reactions were combined and poured into water (200 mL), extracted with dichloromethane (2×200 mL). The organic layer was washed with brine (200 mL), dried over anhydrous sodium sulfate, filtered, and concentrated under reduced pressure. The residue was purified by column chromatography on silica gel, eluting with 25% ethyl acetate in petroleum ether to give the title compound. $^1$H NMR (501 MHz, CDCl$_3$) δ ppm 7.61 (dd, 1H), 7.43 (d, 1H), 7.00 (s, 1H), 6.85 (d, 1H), 6.05 (s, 2H), 2.62 (s, 6H). MS (ESI+) m/z 328.2 (M+H)$^+$.

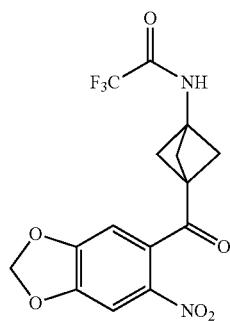

Example 1D 2,2,2-trifluoro-N-(3-(6-nitrobenzo[d][1,3]dioxole-5-carbonyl)bicyclo[1.1.1]pentan-1-yl)acetamide To a solution of Example 1C (4.3 g) in acetic anhydride (25 mL) was added copper(II) nitrate trihydrate (4.76 g) in portions at 0° C. The mixture was stirred at 0° C. for 3 hours. Three additional reactions were set up and stirred at 0° C. for 3 hours as described. All four reactions were combined. The mixture was poured into water (50 mL) and extracted with ethyl acetate (5×100 mL). The organic layer was dried over anhydrous sodium sulfate, filtered, concentrated under reduced pressure. The residue was purified by column chromatography on silica gel, eluting with 75% ethyl acetate in petroleum ether to give the title compound. $^1$H NMR (400 MHz, CDCl$_3$) δ ppm 7.61 (s, 1H), 6.77 (br s, 1H), 6.64 (s, 1H), 6.21 (s, 2 H), 2.43 (s, 6 H). MS (APCI+) m/z 373.1 (M+H)$^+$.

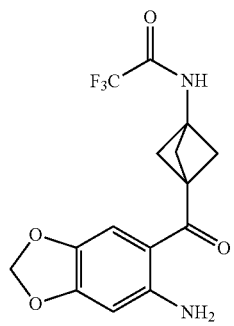 [SMILES: Nc1cc2c(cc1C(=O)C13CC(NC(=O)C(F)(F)F)(C1)C3)OCO2]

18

Example 1E

N-(3-(6-aminobenzo[d][1,3]dioxole-5-carbonyl)bicyclo[1.1.1]pentan-1-yl)-2,2,2-trifluoroacetamide To a solution of Example 1D (4 g) in ethanol (40 mL) and water (8 mL) was added iron (5.4 g) and ammonium chloride (5.17 g) under nitrogen. The mixture was stirred at 100° C. for 3 hours. Three additional reactions were set up and stirred at 100° C. for 3 hours as described. After cooling to ambient temperature, all four reactions were combined. The mixture was poured into water (1 L) and extracted with ethyl acetate (5×500 mL). The combined organic phases were dried over anhydrous sodium sulfate, filtered, and concentrated under reduced pressure. The residue was purified by column chromatography on silica gel, eluting with 10-75% ethyl acetate in petroleum ether to give the title compound. $^{1H}$ NMR (400 MHz, CDCl$_3$) δ ppm 7.22 (s, 1H), 6.70 (s, 1H), 6.50 (s, 2H), 6.14 (s, 1H), 5.92 (s, 2H), 2.63 (s, 6H). MS (ESI+) m/z 343.2 (M+H)$^+$.

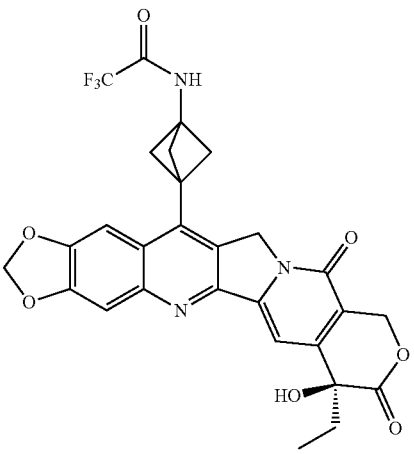 [SMILES: CC[C@@]1(O)C(=O)OCc2c1cc1n(c2=O)Cc2c-1nc1cc3c(cc1c2C12CC(NC(=O)C(F)(F)F)(C1)C2)OCO3]

Example 1F (S)-N-(3-(7-ethyl-7-hydroxy-8,11-dioxo-8,10,11,13-tetrahydro-7H-[1,3] dioxolo[4,5-g]pyrano[3',4':6,7]indolizino[1,2-b]quinolin-14-yl)bicyclo[1.1.1]pentan-1-yl)-2,2,2-trifluoroacetamide To a suspension of Example 1E (3.5 g) and (S)-4-ethyl-4-hydroxy-7,8-dihydro-1H-pyrano[3,4-f]indolizine-3,6,10(4H)-trione (2.69 g) in toluene (140 mL) was added para-toluenesulfonic acid monohydrate (1.945 g). The mixture was stirred at 115° C. for 12 hours. Three additional reactions were set up and stirred at 115° C. for 12 hours as described. After cooling to ambient temperature, all four reactions were combined. The mixture was filtered and the solid collected was triturated with acetonitrile (200 mL) to give the title compound. $^1$H NMR (400 MHz, dimethyl sulfoxide-d$_6$) δ ppm 10.28 (s, 1H), 7.64 (s, 1H), 7.52 (s, 1H), 7.24 (s, 1H), 6.47 (s, 1H), 6.30 (dd, 2H), 5.42 (s, 2H), 5.36 (s, 2H), 2.87 (s, 6H), 1.94-1.77 (m, 2H), 0.88 (t, 3H). MS (ESI+) m/z 570.3 (M+H)$^+$.

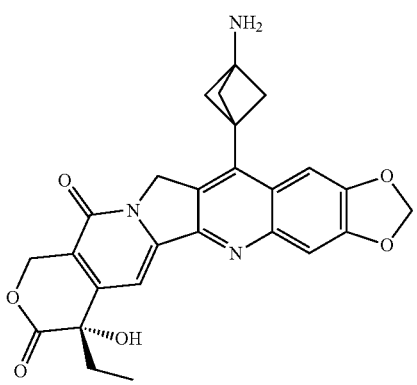

Example 1G (7S)-14-(3-aminobicyclo[1.1.1]pentan-1-yl)-7-ethyl-7-hydroxy-2H,10H-[1,3]dioxolo[4,5-g]pyrano[3',4':6,7]indolizino[1,2-b]quinoline-8,11(7H,13H)-dione To a solution of Example 1F (3 g) in methanol (30 mL) was added HCl (60 mL, 4 M in methanol). The mixture was stirred at 65° C. for 4 hours. Four additional reactions were set up and stirred at 65° C. for 4 hours as described above. After cooling to ambient temperature, all five reactions were combined. The mixture was concentrated under reduced pressure and the residue was triturated with methanol (200 mL) to give the title compound. $^1$H NMR (400 MHz, dimethyl sulfoxide -$d_6$) δ ppm 9.23 (s, 3H), 7.54 (s, 1H), 7.51 (s, 1H), 7.24 (s, 1H), 6.30 (d, 2H), 5.41 (s, 2H), 5.39-5.26 (m, 2H), 2.79 (s, 6H), 1.87 (hept, 2H), 0.88 (t, 3H). MS (ESI+) m/z 474.3 (M+H)$^+$.

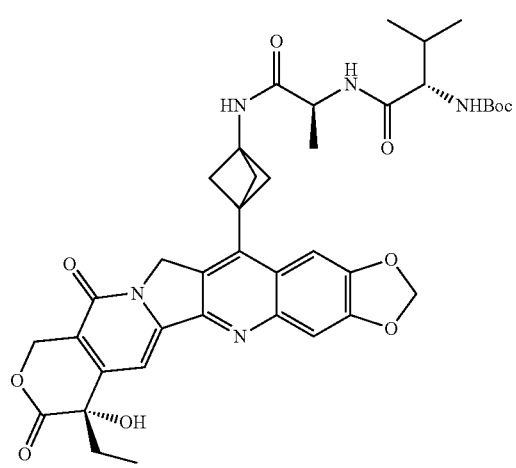 [SMILES: CC[C@@]1(O)C(=O)OCc2c1cc1n(c2=O)Cc2c-1nc1cc3c(cc1c2C12CC(NC(=O)[C@H](C)NC(=O)[C@@H](NC(=O)OC(C)(C)C)C(C)C)(C1)C2)OCO3]

Example 1H tert-butyl ((S)-1-(((S)-1-((3-((S)-7-ethyl-7-hydroxy-8, 11-dioxo-8, 10,11,13-tetrahydro-7H-[1,3]dioxolo [4,5-g]pyrano[3',4':6,7]indolizino[1,2-b] quinolin-14-yl)bicyclo [1.1.1]pentan-1-yl)amino)-1-oxopropan-2-yl)amino)-3-methyl-1-oxobutan-2-yl) carbamate To a suspension of (S)-24(S)-2-((tert-butoxycarbonyl)amino)-3-methylbutanamido)propanoic acid (2.49 g), 2-hydroxypyridine 1-oxide (1.31 g), and $N^1$-((ethylimino)methylene)-$N^3$,$N^3$-dimethylpropane-1,3-diamine hydrochloride (2.26 g) in acetonitrile (40 mL) was added 2,6-lutidine (2.74 mL). The mixture was stirred at ambient temperature for 30 minutes. In a separate flask, Example 1G (4 g) and 2,6-lutidine (2.74 mL) were combined in N,N-dimethylformamide (40 mL) and the above solution was added. The mixture was stirred at ambient temperature overnight. The mixture was concentrated under reduced pressure and the residue was dissolved in dichloromethane (300 mL), washed with saturated aqueous ammonium chloride solution (100 mL), brine (100 mL), dried over anhydrous sodium sulfate, filtered, and concentrated under reduced pressure. The residue was purified by column chromatography on silica gel, eluting with 0-10% methanol in dichloromethane to give the title compound. $^1$H NMR (400 MHz, dimethyl sulfoxide -$d_6$) δ ppm 8.65 (s, 1H), 7.89 (d, 1H), 7.61 (s, 1H), 7.49 (s, 1H), 7.22 (s, 1H), 6.77 (d, 1H), 6.46 (s, 1H), 6.29 (d, 2H), 5.41 (s, 2H), 5.32 (s, 2H), 4.29 (q, 1H), 3.87-3.77 (m, 1H), 2.76 (s, 6H), 1.99 (q, 1H), 1.92-1.81 (m, 2H), 1.41 (s, 9H), 1.25 (d, 3H), 0.92-0.80 (m, 9H). MS (ESI+) m/z 744.4 (M+H)$^+$.

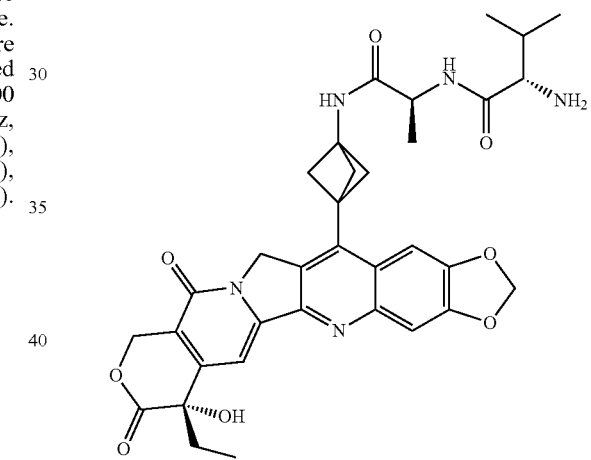

Example 1I (S)-2-amino-N-((S)-1-((3-((S)-7-ethyl-7-hydroxy-8, 11-dioxo-8,10,11,13-tetrahydro-7H-[1,3]dioxolo[4, 5-g]pyrano[3',4':6,7]indolizino[1,2-b]quinolin-14-yl) bicyclo [1.1.1]pentan-1-yl)amino)-1-oxopropan-2-yl)-3-methylbutanamide Example 1H (5.5 g) was treated with trifluoracetic acid (30 mL) at ambient temperature for 30 minutes. The mixture was concentrated under reduced pressure and the residue was dissolved in 50% acetonitrile in water (200 mL). The solution was lyophilized to give the title compound. $^1$H NMR (600 MHz, dimethyl sulfoxide -$d_6$) δ ppm 8.80 (s, 1H), 8.59 (d, 1H), 8.10 (d, 3H), 7.60 (s, 1H), 7.48 (s, 1H), 7.23 (s, 1H), 6.33-6.26 (m, 2H), 5.41 (d, 2H), 5.35-5.23 (m, 2H), 4.35 (p, 1H), 3.66-3.63 (m, 1H), 2.77 (s, 6H), 2.17-2.06 (m, 1H), 1.91-1.83 (m, 2H), 1.31 (d, 3H), 1.01-0.96 (dd, 6H), 0.89 (t, 3H). MS (ESI+) m/z 644.4 (M+H)+.

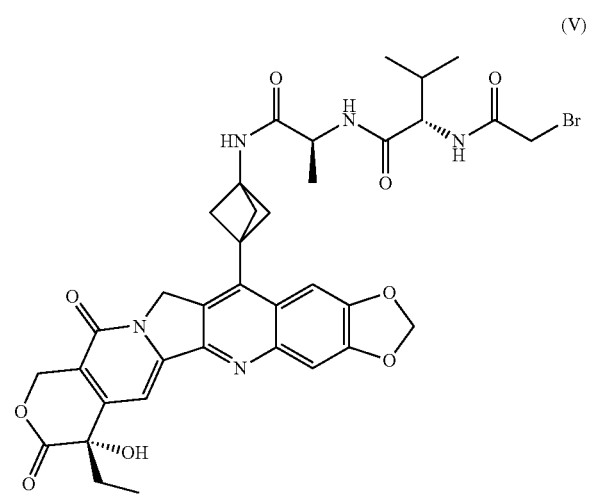 [SMILES: CC[C@@]1(O)C(=O)OCc2c1cc1n(c2=O)Cc2c-1nc1cc3c(cc1c2C12CC(NC(=O)[C@H](C)NC(=O)[C@@H](NC(=O)CBr)C(C)C)(C1)C2)OCO3]

(V)

Example 1J (2S)-2-(2-bromoacetamido)-N-[(2S)-1-({3-[(7S)-7-ethyl-7-hydroxy-8,11-dioxo-7,8,11,13-tetrahydro-2H,10H-[1,3]dioxolo[4,5-g]pyrano[3',4':6,7]indolizino[1,2-b]quinolin-14-yl]bicyclo [1.1.1]pentan-1-yl}amino)-1-oxopropan-2-yl]-3-methylbutanamide To a solution of 2-bromoacetic acid (1.435 g) in N,N-dimethylformamide (26 mL) was added ethyl 2-ethoxyquinoline-1(2H)-carboxylate (2.55 g). The mixture was stirred at ambient temperature for 10 minutes. In a separate flask, Example 1I (4.5 g) and 2,6-lutidine (3.61 mL) were combined in N,N-dimethylformamide (26 mL) and the above solution was added. The mixture was stirred at ambient temperature for 30 minutes. The mixture was acidified with trifluoroacetic acid (4 mL) and purified by reversed-phase HPLC on a CombiFlash® Teledyne Isco system using a Luna column (250×50 mm, 10 mm), eluting with 5-75% acetonitrile in water containing 0.1% trifluoroacetic acid over 30 minutes to give the title compound after lyophilization. $^1$H NMR (600 MHz, dimethyl sulfoxide-$d_6$) δ ppm 8.57 (s, 1H), 8.32 (d, 1H), 8.16 (d, 1H), 7.67 (s, 1H), 7.52 (s, 1H), 7.24 (s, 1H), 6.30 (dd, 2H), 5.42 (s, 2H), 5.38 (d, 2H), 4.28-4.19 (m, 2H), 4.03-3.91 (m, 2H), 2.76 (s, 6H), 2.02 (h, 1H), 1.86 (ddp, 2H), 1.25 (d, 3H), 0.93-0.84 (m, 9H). MS (ESI+) m/z 764.46 (M+H)+.

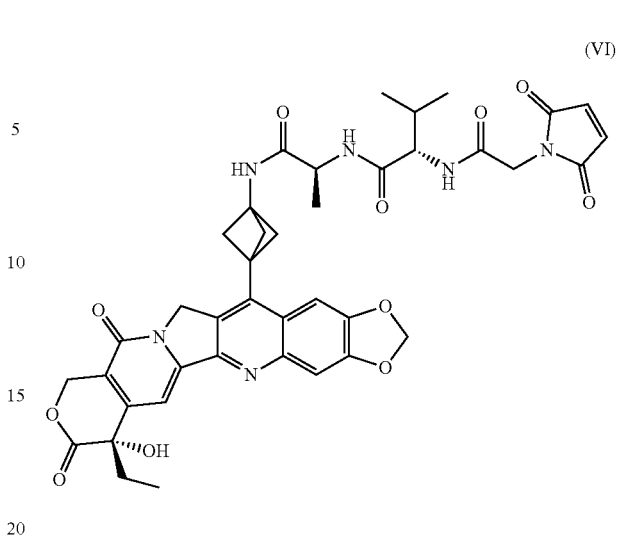

(VI)

Example 2

(2S)-2-[2-(2,5-dioxo-2,5-dihydro-1H-pyrrol-1-yl)acetamido]-N-[(2S)-1-({3-[(7S)-7-ethyl-7-hydroxy-8,11-dioxo-7,8,11,13-tetrahydro-2H,10H-[1,3]dioxolo[4,5-g]pyrano[3',4':6,7]indolizino[1,2-b]quinolin-14-yl]bicyclo[1.1.1]pentan-1-yl}amino)-1-oxopropan-2-yl]-3-methylbutanamide A solution of Example 1I (2 g) in N,N-dimethylformamide (54 mL) was added 2,5-dioxopyrrolidin-1-yl 2-(2,5-dioxo-2,5-dihydro-1H-pyrrol-1-yl)acetate (0.7 g) followed by N,N-diisopropylethylamine (2.3 mL). The mixture was stirred at ambient temperature for 30 minutes. The reaction was quenched with trifluoroacetic acid (2 mL) and purified by reversed-phase HPLC on a Gilson PLC 2020 system using a Luna column (250×50 mm, 10 mm), eluting with 5-75% acetonitrile in water containing 0.1% trifluoroacetic acid over 30 minutes to provide the title compound after lyophilization. $^1$H NMR (500 MHz, dimethyl sulfoxide -$d_6$) δ ppm 8.50 (s, 1H), 8.29 (d, 1H), 8.13 (d, 1H), 7.64 (s, 1H), 7.51 (s, 1H), 7.23 (s, 1H), 7.12 (s, 2H), 6.30 (d, 2H), 5.42 (s, 2H), 5.36 (d, 2H), 4.24 (p, 1H), 4.20-4.14 (m, 3H), 2.75 (s, 6H), 2.01 (h, 1H), 1.86 (dp, 2H), 1.26 (d, 3H), 0.93-0.83 (m, 9H). MS (ESI+) m/z 781.14 (M+H)+.

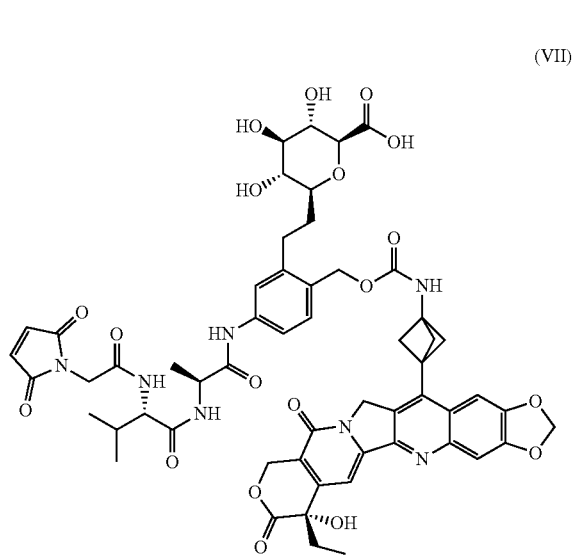 [SMILES: CC[C@@]1(O)C(=O)OCc2c1cc1n(c2=O)Cc2c-1nc1cc3c(cc1c2C12CC(NC(=O)OCc4ccc(NC(=O)[C@H](C)NC(=O)[C@@H](NC(=O)CN5C(=O)C=CC5=O)C(C)C)cc4CC[C@@H]4O[C@H](C(=O)O)[C@@H](O)[C@H](O)[C@H]4O)(C1)C2)OCO3]

(VII)

Example 3

(2S,3S,4R,5R,6S)-6-[2-(5-{[(2S)-2-({(2S)-2-[2-(2,5-dioxo-2,5-dihydro-1H-pyrrol-1-yl)acetamido]-3-methylbutanoyl}amino)propanoyl]amino}-2-{[({3-[(7S)-7-ethyl-7-hydroxy-8,11-dioxo-7,8,11,13-tetrahydro-2H,10H-[1,3]dioxolo[4,5-g]pyrano[3',4':6,7]indolizino[1,2-b]quinolin-14-yl]bicyclo[1.1.1]pentan-1-yl}carbamoyl)oxy]methyl}phenyl)ethyl]-3,4,5-trihydroxyoxane-2-carboxylic acid

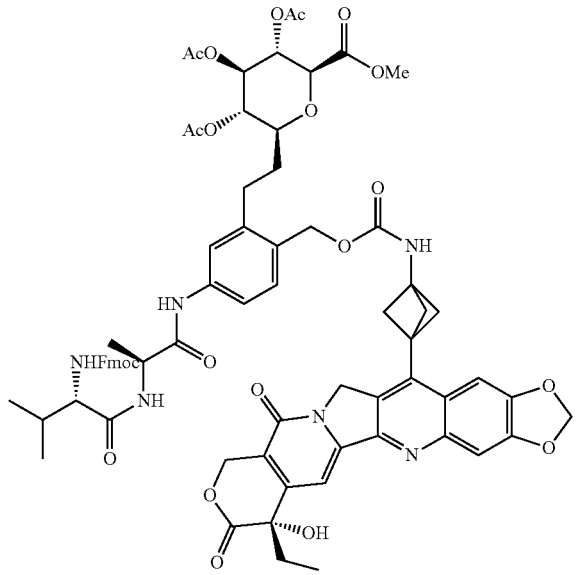

Example 3A (2S,3S,4R,5S,6S)-2-(5-((S)-2-((((9H-fluoren-9-yl)methoxy)carbonyl)amino)-3-methylbutanamido)propanamido)-2-((((3-((S)-7-ethyl-7-hydroxy-8,11-dioxo-8,10,11,13-tetrahydro-7H-[1,3]dioxolo[4,5-g]pyrano[3',4':6,7]indolizino[1,2-b]quinolin-14-yl)bicyclo[1.1.1]pentan-1-yl)carbamoyl)oxy)methyl)phenethyl)-6-(methoxycarbonyl)tetrahydro-2H-pyran-3,4,5-triyl triacetate To a mixture of (2S,3S,4R,5S,6S)-2-(5-((S)-2-((S)-2-((((9H-fluoren-9-yl)methoxy)carbonyl)amino)-3-methylbutanamido)propanamido)-2-((((4-nitrophenoxy)carbonyloxy)methyl)phenethyl)-6-(methoxycarbonyl)tetrahydro-2H-pyran-3,4,5-triyl triacetate (prepared as described in WO2016094509, 2.99 g), Example 1G (1.35 g) and 1-hydroxy-7-azabenzotriazole (0.361 g) in N,N-dimethylformamide (26.5 mL) was added N,N-diisopropylethylamine (1.39 mL). The mixture was stirred at ambient temperature for 4 hours. The mixture was concentrated under reduced pressure and the residue was purified by column chromatography on silica gel, eluting with 0-8% methanol in dichloromethane to give the title compound. $^1$H NMR (501 MHz, CDCl$_3$) δ ppm 8.43 (br s, 1H), 7.74 (d, 2H), 7.61 (br s, 1H), 7.57-7.46 (d, 4H), 7.43 (s, 1H), 7.38 (t, 3H), 7.33-7.27 (m, 3H), 6.43 (br s, 1H), 6.17 (s, 2H), 5.89 (br s, 1H), 5.72 (d, 1H), 5.37-5.02 (m, 8H), 4.94 (t, 1H), 4.67-4.56 (m, 1H), 4.53-4.44 (t, 2H), 4.19 (br s, 1H), 4.00 (d, 2H), 3.77 (s, 3H), 3.48 (dt, 1H), 2.94 (d, 1H), 2.88-2.66 (m, 6H), 2.16 (br s, 1H), 2.08-1.97 (m, 9H), 1.94-1.80 (ddt, 4H), 1.45 (d, 3H), 1.02 (t, 3H), 0.98-0.90 (m, 6H). MS (ESI+) m/z 1359.5 (M+H)$^+$.

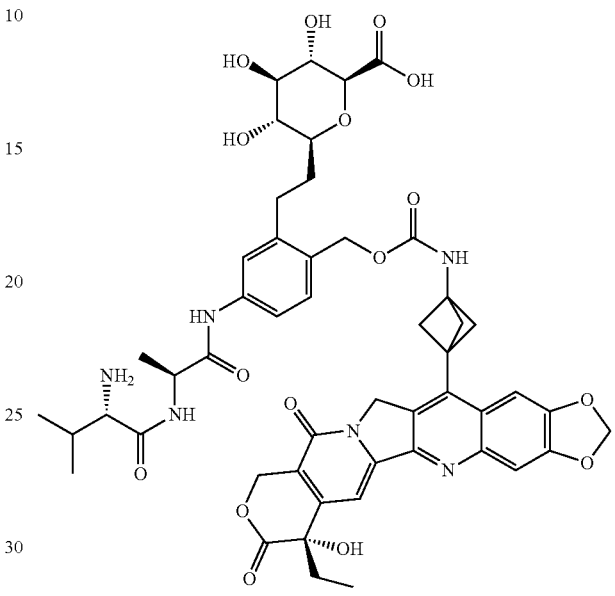

Example 3B (2S,3S,4R,5R,6S)-6-(5-((S)-2-((S)-2-amino-3-methylbutanamido)propanamido)-2-((((3-((S)-7-ethyl-7-hydroxy-8,11-dioxo-8,10,11,13-tetrahydro-7H-[1,3]dioxolo[4,5-g]pyrano[3',4':6,7]indolizino[1,2-b]quinolin-14-yl)bicyclo[1.1.1]pentan-1-yl)carbamoyl)oxy)methyl)phenethyl)-3,4,5-trihydroxytetrahydro-2H-pyran-2-carboxylic acid To a solution of Example 3A (3.2 g) in methanol (24 mL) and tetrahydrofuran (24 mL) was added lithium hydroxide monohydrate (846 mg) in water (24 mL). The mixture was stirred at ambient temperature for 30 minutes. The reaction was quenched with trifluoracetic acid (3 mL) and extracted with heptane (5×30 mL). The aqueous layer was purified by reversed-phase HPLC on a CombiFlash® Teledyne Isco system using a Luna column (250×50 mm, 10 mm), eluting with 5-75% acetonitrile in water containing 0.1% trifluoroacetic acid over 30 minutes to provide the title compound after lyophilization. $^1$H NMR (400 MHz, dimethyl sulfoxide-d$_6$) δ ppm 10.03 (s, 1H), 8.62 (d, 1H), 8.02 (br s, 4H), 7.55 (s, 1H), 7.43 (s, 1H), 7.41 (d, 2H), 7.35 (s, 1H), 7.22 (d, 1H), 7.16 (s, 1H), 6.40 (br s, 1H), 6.23 (s, 2H), 5.35 (s, 2H), 5.27 (s, 2H), 4.97 (s, 2H), 4.43 (p, 1H), 3.60-3.47 (m, 3H), 3.15-3.01 (m, 3H), 2.90 (t, 1H), 2.64 (s, 6H), 2.00 (tq, 2H), 1.79 (hept, 2H), 1.60-1.46 (m, 1H), 1.29 (d, 3H), 0.89 (dd, 6H), 0.80 (t, 3H). MS (ESI+) m/z 997.3 (M+H)$^+$.

(VII)

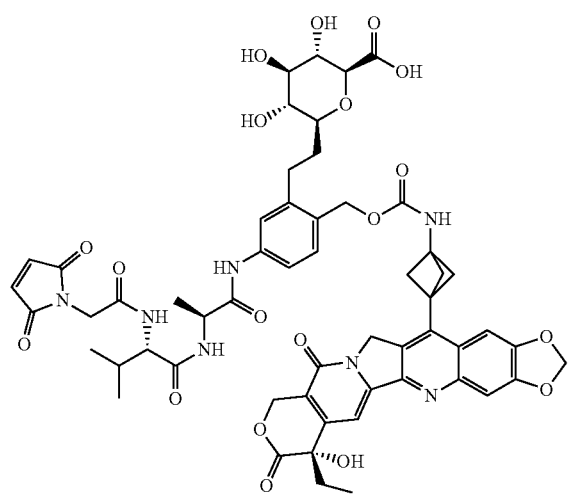

Example 3C (2S,3S,4R,5R,6S)-6-[2-(5-{[(2S)-2-({(2S)-2-[2-(2,5-dioxo-2,5-dihydro-1H-pyrrol-1-yl)acetamido]-3-methylbutanoyl}amino)propanoyl]amino}-2-{[({3-[(7S)-7-ethyl-7-hydroxy-8,11-dioxo-7,8,11,13-tetrahydro-2H,10H-[1,3]dioxolo[4,5-g]pyrano[3',4': 6,7]indolizino[1,2-b]quinolin-14-yl]bicyclo[1.1.1] pentan-1-yl}carbamoyl)oxy]methyl}phenyl)ethyl]-3, 4,5-trihydroxyoxane-2-carboxylic acid A solution of Example 3B (1.02 g) in N,N-dimethylformamide (16 mL) was added 2,5-dioxopyrrolidin-1-yl 2-(2, 5-dioxo-2,5-dihydro-1H-pyrrol-1-yl)acetate (0.28 g) followed by N,N-diisopropylethylamine (0.8 mL). The mixture was stirred at ambient temperature for 30 minutes. The reaction was quenched with acetic acid (0.8 mL) and purified by reversed-phase HPLC on a Gilson PLC 2020 system using a Luna column (250×50 mm, 10 mm), eluting with 5-75% acetonitrile in water containing 0.1% trifluoroacetic acid over 30 minutes to provide the title compound after lyophilization. $^1$H NMR (501 MHz, dimethyl sulfoxide -$d_6$) δ ppm 9.90 (s, 1H), 8.29-8.25 (m, 2H), 8.11 (s, 1H), 7.64 (s, 1H), 7.51 (s, 1H), 7.47 (d, 1H), 7.42 (s, 1H), 7.27 (d, 1H), 7.23 (s, 1H), 7.08 (s, 2H), 6.30 (s, 2H), 5.42 (s, 2H), 5.36 (s, 2H), 5.03 (s, 2H), 4.38 (p, 1H), 4.22 (dd, 1H), 4.13 (s, 2H), 3.58 (d, 2H), 3.15 (d, 4H), 2.97 (t, 1H), 2.71 (s, 6H), 2.10-1.93 (m, 2H), 1.86 (dp, 2H), 1.64-1.52 (m, 1H), 1.31 (d, 3H), 0.91— 0.79 (m, 9H). MS (ESI+) m/z 1134.3 (M+H)$^+$.

Example 4

Cell Proliferation

The effect of TOP1i drugs on cell viability was assessed by monitoring ATP presence for metabolically active cells. Proliferation of Calu-6 cells (lung adenocarcinoma) and A375 cells (malignant melanoma) were quantified using CellTiter-Glo® luminescence. As shown in FIG. 2A and in Table 1, the compound of Formula I (Example 1G) exhibited sub-nanomolar potency for reducing viability of proliferating Calu-6 cells (0.57 nM, FIG. 2A) and A375 (0.50 nM, FIG. 2B). This sub-nanomolar potency improved over performance of the TOP1i drug SN-38 in the same assay, which demonstrated an $EC_{50}$ of 6.58 nM (Calu-6) and 2.30 nM (A375).

TABLE 1

| | TOP1i Compound Potency | |
|---|---|---|
| | $EC_{50}$ (nM) | |
| Compound | Calu-6 | A375 |
| SN-38 | 6.58 | 2.30 |
| Example 1G | 0.57 | 0.50 |

(IV)

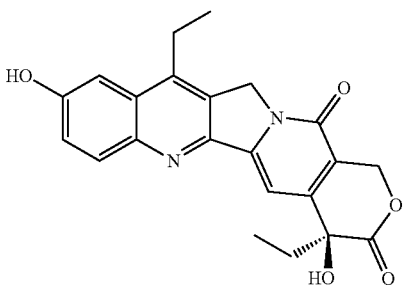

SN-38

Example 5

Preparation and Purification of AbA

AbA was expressed in Chinese hamster ovary (CHO) cells with the heavy and light chain sequences of SEQ ID NOS: 9 and 10, respectively. AbA was isolated and purified prior to conjugation.

Example 6

Procedure for Conjugation (ADC-1)

Conjugation Step 1

Prior to reduction, a solution of anti-c-Met antibody AbA was incubated at 4° C. for a minimum of 12 hours. A 0.5 M ethylenediaminetetraacetic acid disodium salt solution (EDTA, Sigma Aldrich) was then added, for a final concentration of 5 mM. Tris (2-carboxyethyl) phosphine (TCEP, 100 mM, 2.67 molar equivalents, Bond Breaker™, Thermo Scientific™) was added to the solution (approximately 10 mg/mL in 1×DPBS (Dulbecco's phosphate-buffered saline) with gentle stir plate mixing (225 rpm) for 5 minutes. Following refrigerator incubation at 4° C. for 17 hours, the solution was brought to 22° C. on a stir plate mixing at 225 rpm. A 10% v/v N,N-dimethylacetamide (DMA, Sigma Aldrich) co-solvent was then added, followed by 20% v/v of prepared 1 M boric acid, pH 8.0 (Sigma Aldrich) and then 6 mol equivalents of 50 mM linker drug LD1 (structural formula V, Example 1J) in N,N-dimethylacetamide, dropwise. Mixing was discontinued after 20 minutes and the solution was incubated at 22° C. for 3.3 hours. Following incubation, 2 mol equivalents of 50 mM N-Acetyl-L-cysteine (NAC, Sigma Aldrich) prepared in 1×DPBS, were added to the solution, and gently mixed by manually agitating the vessel. Following a 1-hour incubation at 22° C., the solution was desalted using a 691 mL G25 Fine Desalting (Cytiva™) Column, into 1×DPBS.

Conjugation Step 2

Prior to reduction, a solution of anti-c-Met antibody AbA was incubated at 4° C. for a minimum of 12 hours. A 0.5 M ethylenediaminetetraacetic acid disodium salt solution (EDTA, Sigma Aldrich) was then added, for a final concentration of 5 mM. Tris (2-carboxyethyl) phosphine (TCEP, 100 mM, 1.00 mol eq, Bond Breaker™, Thermo Scientific™) was added to a solution of antibody (approximately 4 mg/mL in 1×DPBS) with gentle stir plate mixing (225 rpm) for 5 minutes. Following refrigerator incubation at 4° C. for 17 hours, the solution was brought to 22° C. on a stir plate mixing at 225 rpm. A 10% v/v N,N-dimethylacetamide (DMA, Sigma Aldrich) co-solvent was then added, followed by 20% v/v 1 M boric acid, pH 8.0 (Sigma Aldrich) and then 4 molar equivalents of 50 mM linker drug LD1 (structural formula V, Example 1J) in N,N-dimethylacetamide, dropwise. Mixing was discontinued after 20 minutes and the solution was incubated at 22° C. for 2.1 hours. Following incubation, 2 molar equivalents of 10 mM N-acetyl-L-cysteine (NAC, Sigma Aldrich), prepared in 1×DPBS, were added to the solution, and gently mixed by manually agitating the vessel. Following a 5-hour incubation at 22° C., the solution was concentrated, and buffer exchanged via Ultrafiltration Diafiltration (UF/DF).

UF/DF Step

A Pellicon® 3 0.22 m² Cassette (Millipore) was flushed with 2 L of sterile water and then 0.5 L of formulation buffer. Ultrafiltration (UF) was performed at 250 mL/minute feed flow rate, and a Transmembrane Pressure (™P) of 12-13 psi, with a starting volume of 1.3 L. Final permeate volume was 1.1 L. Diafiltration (DF) was performed with 25 diavolumes (DV) of final formulation buffer, at the same feed flow rate and TMP as the UF step. Following DF, a second UF step was performed to further reduce ADC solution volume to 100 mL. The ADC solution was removed, and the cassette was twice rinsed and with 125 mL of formulation buffer which was then ultrafiltered to 20 mL each. These rinses were then added to the bulk ADC solution. The final solution was sterile filtered with a 0.22 µm filter, prior to characterization.

Example 7

Procedure for Conjugation (ADC-2)

Prior to reduction, a solution of anti-c-Met antibody AbA was incubated on wet ice for 35 minutes. A 0.5 M ethylenediaminetetraacetic acid disodium salt solution (EDTA, Sigma Aldrich) was then added, for a final concentration of 5 mM. Tris (2-carboxyethyl) phosphine (TCEP, 25 mM, 3.50 molar equivalent, Bond Breaker™, Thermo Scientific™) was added to the solution (approximately 10 mg/mL in 1×DPBS) and gently mixed by slowly inverting the tube several times. The solution was then placed on wet ice and placed in the 4° C. refrigerator for 24 hours. Following incubation, 10% v/v N,N-dimethylacetamide co-solvent was added followed by 10 molar equivalents of 10 mM linker drug LD2 (structural formula VI, Example 2) in N,N-dimethylacetamide (DMA, Sigma Aldrich) solution, and gently mixed by slowly inverting the tube several times. The solution was then placed on wet ice for 30 minutes and incubated at 22° C. for 90 minutes. Following incubation, 8 molar equivalents of 10 mM N-acetyl-L-cysteine (NAC, Sigma Aldrich) prepared in PBS were added to the solution, and gently mixed by slowly inverting the tube several times. After a 60-minute incubation at 22° C., the solution was desalted over a HiPrep™ 26/10 desalting column into 1×DPBS (Cytiva™). Desalted ADCs were then hydrolyzed by the addition of a prepared solution of 10% v/v 1 M boric acid, pH 8.0 (Sigma Aldrich) with a 22° C. incubation, for 96 hours. Hydrolyzed ADCs were purified through coupled affinity to desalting chromatography (2×1 mL HiTrap MabSelect SuRe, HiPrep™ 26/10 desalting, Cytiva™) into a final formulation of 1×DPBS. Collected fractions were pooled and sterile filtered through a 0.22 µm filter prior to characterization.

Example 8

Procedure for Conjugation (ADC-3)

Aqueous ethylenediaminetetraacetic acid disodium salt (EDTA, 0.5 M, 21.3 µL, Sigma Aldrich) was added to 5.337 mL of a solution of anti-c-Met antibody (AbA, 13.34 mg/mL in 1×DPBS, pH 7.4). Tris(2-carboxyethyl) phosphine (TCEP, 10 mM, 3.0 molar eq, 142.4 µL, Bond Breaker™, Thermo Scientific™) was added to the solution, gently stirred, and kept at 37° C. for 75 minutes. The solution was cooled to ambient temperature and linker-drug LD3 (structural formula VII, Example 3C) was added (10 eq., 527 µL of 10 mM solution of LD3 (Structural Formula VII, Example 3C in N,N-dimethylacetamide, 90% purity)). The conjugation was gently stirred and allowed to stand for 1.2 hours at ambient temperatige. The ADC solution was purified by desalting. After desalting, the ADC solution was filtered through 0.22 µm filter and resulting sample stored at 4° C. The resultant ADC was hydrolyzed by adding 10% v/v 1.0 M borate buffer, pH 8.0 and incubated in a dark environment at ambient temperature for 72 hours. After hydrolysis, the resultant ADC solution was purified by adsorbing to a protein A resin column (MabSelect™ SuRe™ LX, GE Healthcare); washing with 4 column volumes of 1×DPBS, pH 7.4; eluting off resin with 5 column volumes of IgG Elution Buffer (Thermo Scientific™); and desalted into 1×DPBS, pH 7.4. After desalting, the ADC solution was filtered through a 0.22 µm filter and the resulting sample was stored at 4° C.

Example 9

Procedure for Conjugation (ADC-4)

Aqueous ethylenediaminetetraacetic acid disodium salt (EDTA, 0.5 M, 974 µL, Sigma Aldrich) was added to 243.3 mL of a purified solution of MSL109-C6v1 antibody (12.3 mg/mL in 20 mM Tris buffer, pH 7.4). MSL109-C6v1 is a monoclonal antibody that binds to CMV glycoprotein H. MSL109-C6v1 comprises a heavy chain set forth as SEQ ID NO: 11 and a light chain set forth as SEQ ID NO: 12 and is used as a non-targeting control antibody. Tris(2-carboxyethyl) phosphine (TCEP, 500 mM, 6.0 molar eq, 242.4 µL, Bond Breaker™, Thermo Scientific™) was added to the solution of MSL109-C6v1 with 2 mM EDTA, and gently stirred and kept at 4° C. for 20 hours. Tris buffer at 4° C. (1.0 M, pH 8.0) was added to the solution (24.5 mL, 10% v/v). The linker-drug LD1 (Example 1J, (2S)-2-(2-bromoacetamido)-N-[(2S)-1-({3-[(7S)-7-ethyl-7-hydroxy-8,11-dioxo- 7,8,11,13-tetrahydro-2H,10H-[1,3]dioxolo[4,5-g]pyrano[3',4':6,7]indolizino[1,2-b]quinolin-14-yl]bicyclo[1.1.1]pentan-1-yl}amino)-1-oxopropan-2-yl]-3-methylbutanamide) was added to the reduced antibody at pH 8.0 (10 equivalents, 22.5 mL of 10 mM solution of LD1, structural formula V, Example 1J, in N,N-dimethylacetamide, 90% purity). The conjugation was gently stirred and allowed to stand for 1.5 hours in an ambient temperature water bath. The conjugation was quenched with addition of 4 equivalents of an aqueous solution of N-acetyl-L-cysteine (NAC, Sigma Aldrich, 100 mM solution in 1×DPBS, 0.8 mL). The mixture was gently stirred and allowed to stand for 1 hour at ambient temperature. Tris buffer (15%, Sigma, 1.0 M, pH 7.4, 44 mL) was added to adjust the ADC solution to pH 7.5. The ADC solution was stored at 4° C. overnight. The ADC solution was concentrated, and buffer exchanged via Ultrafiltration Diafiltration (Pellicon® 3 0.22 m² Cassette (Millipore)). The final ADC solution was filtered through a 0.22 μm filter and the resulting ADC sample stored at 4° C. Final volume of ADC was 138 mL.

Example 10

DAR (Drug Antibody Ratio) Determination

DAR was determined by LC-MS. LC-MS analysis was performed using an Agilent 1100 HPLC system interfaced to an Agilent LC/MSD TOF 6220 ESI mass spectrometer. The ADC was reduced with 5 mM (final concentration) Bond-Breaker™ TCEP solution (Thermo Scientific™, Rockford, Ill.), loaded onto a Protein Microtrap (Michrom Bioresources, Auburn, Calif.) desalting cartridge, and eluted with a gradient of 10% B to 75% B in 0.2 minutes at ambient temperature. Mobile phase A was $H_2O$ with 0.1% formic acid (FA), mobile phase B was acetonitrile with 0.1% FA, and the flow rate was 0.2 mL/minute. Electrospray-ionization time-of-flight mass spectra of the co-eluting light and heavy chains were acquired using Agilent MassHunter™ acquisition software. The extracted intensity vs. m/z spectrum was deconvoluted using the Maximum Entropy feature of MassHunter™ software to determine the mass of each reduced antibody fragment. DAR was calculated from the deconvoluted spectrum by summing intensities of the naked and modified peaks for the light chain and heavy chain, normalized by multiplying intensity by the number of drugs attached. The summed, normalized intensities were divided by the sum of the intensities, and the summing results for two light chains and two heavy chains produced a final average DAR value for the full ADC. Thiosuccinimide hydrolysis of a bioconjugate can be monitored by electrospray mass spectrometry since the addition of water to the conjugate results in an increase of 18 Daltons to the observable molecular weight of the conjugate.

Example 11

Cytotoxicity Assay In Vitro

Tumor cells were plated at 2000-5000 cells/well in 180 μL growth medium containing 10% FBS (fetal bovine serum) in 96-well plates and cultured at 37° C. in a humidified incubator with 5% $CO_2$. After 18 to 24 hours, titrations of antibodies or ADCs in 20 μL were added and cells were incubated for 6 days except for HCC827, NCI-H820, and HEK-293 (5 days) and MIA PaCa2 (4 days). Cell viability was determined using a CellTiter-Glo® Luminescent Cell Viability Assay (Promega) according to the manufacturer's instructions. A non-binding, irrelevant negative control ADC (ADC-4, Structural Formula VIII, where Ab is MSL109-C6v1) was also included in all assays to confirm that cell killing was antigen dependent. All ADCs had an approximately equivalent average DAR.

TABLE 2

Antibody Drug Conjugates

| Antibody | Antibody Heavy Chain (SEQ ID NO) | Antibody Light Chain (SEQ ID NO) | ADC Structural Formula | Conjugation Example |
|---|---|---|---|---|
| ADC-1 | AbA | 9 | 10 | VIII | Ex. 6 |
| ADC-2 | AbA | 9 | 10 | IX | Ex. 7 |
| ADC-3 | AbA | 9 | 10 | X | Ex. 8 |
| ADC-4 | MSL109-C6v1 | 11 | 12 | VIII | Ex. 9 |

Example 12

Determination of Receptor Density c-Met cell surface density (antigen binding capacity per cell) was determined by indirect immunofluorescence staining of cell surface antigens on cultured cells using QIFIKIT® (Dako/Agilent). Briefly, cells were harvested from a culture flask as described above for FACS (fluorescence activated cell sorting) analysis, added to a round bottom 96-well plate at 100 μL/well and incubated at 4° C. with 3 μg/mL c-Met antibody m224G11. Wells, treated with an irrelevant mouse monoclonal antibody of the same isotype (mIgG1) at 3μg/mL, were included as controls. Following a one-hour incubation with primary antibody, cells were centrifuged for 3 minutes at 300×g and washed twice with FACS buffer. For the indirect immunofluorescence staining of the QIFIKIT® beads, 100 μL of resuspended beads from Vial 1 (Set-up Beads) and Vial 2 (Calibration Beads) were added to separate wells, centrifuged for 3 minutes at 300×g, and washed once with FACS buffer. All wells were incubated for one hour at 4° C. with 100 μL of the anti-mouse Alexa Fluor® 488 conjugated antibody (Invitrogen, cat. #A-11029) diluted 1:250 in FACS buffer. Cells were centrifuged for 3 minutes at 300×g, washed twice with FACS buffer, and fixed with 100 μL/well of 1% formaldehyde in PBS (phosphate-buffered saline). Data were acquired on a BD™ LSRII flow cytometer and Geomean values for the 5 bead populations were recorded and used to generate a standard curve based on the lot specific antibody molecules per bead. The standard curve was used to assign ABC (Antibody Binding Capacity or number of receptors) to stained cell samples.

Results

To determine a potential correlation of c-Met expression level and sensitivity to ADC-1, a panel of 9 cell lines were tested in proliferation assays in vitro. FACS analysis demonstrated that these cell lines possess a range of c-Met expression levels as quantified via c-Met antibody binding capacity representing the number of cell surface c-Met molecules (TABLE 3). Sensitivity to ADC-1 in the cell proliferation assay was quantified as maximal killing and $IC_{50}$ (TABLE 3). ADC-1 inhibited proliferation of cancer cells that over-express c-Met, including the MET amplified cell lines (TABLE 3). As a comparison, unconjugated AbA inhibited proliferation of cells with MET amplification i.e., Hs 746T, SNU-5, and EBC-1 (FIG. 3A-C), but not cell lines without MET amplification, i.e., NCI-H441, NCI-H1573, HCC827, NCI-H820, and Calu-3, and where ADC-1 was also active (FIG. 3D-H). Neither unconjugated AbA nor ADC-1 was active on low-c-Met expressing cells HEK-293 and MIA PaCa2 (TABLE 3, FIG. 3I and FIG. 3J), suggesting that there is a threshold level of c-Met expression required for significant killing by ADC-1.

TABLE 3

Cell Potency In Vitro

| Tissue | c-Met receptors/cell[a] | Cytotoxicity IC$_{50}$ (nM) | | |
|---|---|---|---|---|
| | | ADC-3 (max[b]) | ADC-2 (max) | ADC-1 (max) |
| NSCLC Adenocarcinoma | | | | |
| NCI-H441 | 197,000 | 0.1 (60%) | 0.1 (70%) | 0.25 (70%) |
| NCI-H441 | 170,000 | 0.2 (85%) | 0.25 (90%) | 0.3 (90%) |
| NCI-H1573 | 116,000 | 1.1 (60%) | 1[c] (40%) | 1[c] (40%) |
| HCC827 | 94,000 | 0.5 (80%) | 0.9 (70%) | 0.85 (70%) |
| NCI-H820 | 70,000 | 0.06 (75%) | 0.16 (75%) | 0.17 (75%) |
| Calu-3 | 60,000 | nd | nd | 20 (30%) |
| Gastric | | | | |
| Hs 746T | 320,000 | 0.050 (40%) | 0.1 (50%) | 0.17 (50%) |
| SNU-5 | 290,000 | nd[e] | nd | 0.19 (90%) |
| Embryonic Kidney | | | | |
| HEK-293 | 27,000 | nd | nd | >60[d] |
| Pancreatic | | | | |
| MIA PaCa-2 | 5000 | >60[d] | >60[d] | >60[d] |

[a]Approximate number of c-Met molecules on cell surface determined by FACS analysis as antibody binding capacity for m224G1 I (the murine parent of AbA) binding at 0.01 mg/mL
[b]Max is maximum percent decrease relative to the untreated control in the proliferation assay.
[c]Estimated due to curve-fitting issues
[d]Not different from control
[e]nd means not determined Example 13 c-Met-Targeting TOP1i ADC Inhibits the Growth of Cancer Xenografts In Vivo

The cell lines, Hs 746T and NCI-H441 were obtained from ATCC (American Type Culture Collection). Cells were maintained in monolayer culture for at most 3 passages according to recommendations of the supplier. A suspension of 2×10$^6$ cells in culture medium mixed with Matrigel® (1:1, volume:volume) was injected subcutaneously in the right flank of female C.B-17 SCID mice to generate xenografts from the gastric carcinoma cell line, Hs 746T. To generate xenografts from the NSCLC cell line, NCI-H441 a suspension of 5×10$^6$ cells in culture medium mixed with Matrigel (1:1, volume:volume) was injected subcutaneously in female SCID/bg mice. Treatment started when the size of the flank tumors was approximately 200 mm$^3$.

Vehicle (0 mg/kg) and four dose levels (Doses A—D, from lowest to highest) were administered. Each animal received a single dose.

FIG. 4A and 4B show ADC-1 inhibited growth of human NSCLC grown as xenografts in immune-compromised mice. Robust growth inhibition is shown after administration of one dose of ADC-1 at Dose C and Dose D, with moderate tumor growth delay after dosing Dose B in both the Hs 746T and NCI-H441 xenografts.

Example 14 c-MET-Targeting TOP1i ADCs Inhibit the Growth of Patient-Derived Cancer Cells In Vivo The NSCLC patient-derived xenograft (PDX) models, LU450, LU120, LU572, LU123, and LU413, were established internally by implanting patient biopsy tissue fragments subcutaneously in female immunodeficient NOD/SCID mice (Charles River Laboratories). Once tumors were established, PDX tumor cells were expanded by dissociation of tumors to cell suspensions, and 5×10$^4$ cells in culture medium were mixed with Matrigel® (1:1, volume:volume) were injected subcutaneously into the mammary fat pad region of female NOD/SCID mice. For efficacy studies, tumor bearing mice were randomized into treatment groups, with each group having equal average tumor volume (130-200 mm$^3$). The c-Met-ADCs were administered as a single dose at six dose levels (doses A-F, from lowest to highest) via intraperitoneal injection. c-Met-targeted efficacy was compared to a similar administration of vehicle. Tumor volumes were measured one to two times weekly, and efficacy was assessed by plotting tumor volume (mm$^3$) versus time to calculate the time to tumor progression (TTP). TTP, expressed in days, is the time after the single dose treatment when tumor regrow to double the size prior to treatment (at randomization). TTP for durable responses (cures) is indicated as the study length with a ">" sign in front of the number.

TABLE 4

In Vivo Activity of ADC-1 and ADC-2 in NSCLC PDX models

| PDX name | ADC-1[1] | TTP (days) |
|---|---|---|
| LU450 | 0 | 3 |
| | 3 | 15 |
| | 10 | 23 |
| LU572 | 0 | 9 |
| | 0.1 | 26 |
| | 0.25 | >78 |
| | 1 | >91 |
| | 3 | >91 |
| LU211 | 0 | 4 |
| | 3 | 41 |

| PDX name | ADC-2 | TTP (days) |
|---|---|---|
| LU450 | 0 | 4 |
| | 5 | 34 |
| | 10 | 45 |
| LU123 | 0 | 8 |
| | 5 | >106 |

| PDX name | ADC-1[1] | TTP (days) |
|---|---|---|
| LU120 | 10 | >113 |
| | 0 | 23 |
| | 5 | >94 |
| | 10 | >112 |
| LU413 | 0 | 11 |
| | 5 | 40 |
| LU413 | 10 | 71 |

[1]0 = vehicle control

An ADC having a structure according to structural formula (VIII) demonstrated improved in vivo toxicity.

| SEQ ID NO: | Description | Sequence |
|---|---|---|
| 1 | AbA CDR-H1 | GYIFTAYT |
| 2 | AbA CDR-H2 | IKPNNGLA |
| 3 | AbA CDR-H3 | ARSEITTEFDY |
| 4 | AbA CDR-L1 | ESVDSYANSF |
| 5 | AbA CDR-L2 | RAS |
| 6 | AbA CDR-L3 | QQSKEDPLT |
| 7 | AbA Heavy Chain Variable Domain | QVQLVQSGAEVKKPGASVKVSCKASGYIFTAYTMHWVRQAPGQGLEWMGWIKPNNGLANYAQKFQGRVTMTRDTSISTAYMELSRLRSDDTAVYYCARSEITTEFDYWGQGTLVTVSS |
| 8 | AbA Light Chain Variable Domain | DIVMTQSPDSLAVSLGERATINCKSSESVDSYANSFLHWYQQKPGQPPKLLIYRASTRESGVPDRFSGSGSGTDFTLTISSLQAEDVAVYYCQQSKEDPLTFGGGTKVEIK |
| 9 | AbA Heavy Chain | QVQLVQSGAEVKKPGASVKVSCKASGYIFTAYTMHWVRQAPGQGLEWMGWIKPNNGLANYAQKFQGRVTMTRDTSISTAYMELSRLRSDDTAVYYCARSEITTEFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDCHCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 10 | AbA Light Chain | DIVMTQSPDSLAVSLGERATINCKSSESVDSYANSFLHWYQQKPGQPPKLLIYRASTRESGVPDRFSGSGSGTDFTLTISSLQAEDVAVYYCQQSKEDPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 11 | MSL109-C6v1 Heavy Chain | EEQVLESGGGLVKPGGSLRLSCAASGFTFSPYSVFWVRQAPGKGLEWVSSINSDSTYKYYADSVKGRFTISRDNAENSIFLQMNSLRAEDTAVYYCARDRSYYAFSSGSLSDYYYGLDVWGQGTTVIVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 12 | MSL109-C6v1 Light Chain | DIVMTQSPLSLSVTPGEPASISCRSSQSLLHTNGYNYLDWYVQKPGQSPQLLIYLASNRASGVPDRFSGSGSGTDFTLKISRVETEDVGVYYCMQALQIPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEA |
| 13 | m224G11 Heavy Chain Variable Domain | EVQLQQSGPELVKPGASVKISCKTSGYIFTAYTMHWVRQSLGESLDWIGGIKPNNGLANYNQKFKGKATLTVDKSSSTAYMDLRSLTSEDSAVYYCARSEITTEFDYWGQGTALTVSS |
| 14 | m224G11-Light Chain Variable Domain | DIVLTQSPASLAVSLGQRATISCRASESVDSYANSFMHWYQQKPGQPPKLLIYRASNLESGIPARFSGSGSRTDFTLTINPVEADDVATYYCQQSKEDPLTFGSGTKLEMK |
| 15 | m224G11 HC CDR1 | GYIFTAYT |
| 16 | m224G11 HC CDR2 | IKPNNGLA |
| 17 | m224G11 HC CDR3 | ARSEITTEFDY |
| 18 | m224G11 LC CDR1 | ESVDSYANSF |
| 19 | m224G11 LC CDR2 | RAS |
| 20 | m224G11 LC CDR3 | QQSKEDPLT |
| 21 | DNA encoding AbA Heavy Chain | atgggatggtcttggatctttctgctgtttctgtctggtactgctggtgtgctgagccaggtccagctggtgcaatccggcgcagaggtgaagaagccagcgcttccgtgaaggtgagctgtaaggcctctggctacattttcacagcatacaccatgcactgggtgaggcaagctcctgggcagggactggagtggatgggatggattaaacccaacaatgggctggccaactacgcccagaaattccagggtagggtcactatgacaagggataccagcatcagcaccgcatatatg |

SEQUENCE LISTING TABLE

| SEQ ID NO: | Description | Sequence |
|---|---|---|
| | | gagctgagcaggctgaggtc tgacgacactgctgtctatt attgcgccaggagcgaaatt acaacagaattcgattactg ggggcagggcaccctggtga ccgtgtcctctgccagcacc aagggcccaagcgtgttccc cctggcccccagcagcaaga gcaccagcggcggcacagcc gccctgggctgcctggtgaa ggactacttccccgagcccg tgaccgtgtcctggaacagc ggagccctcacttctggagt tcataccttcccagcagtat tgcagagcagtggcctgtat tcactgtcttccgtcgtaac agttccatcctccagcctcg ggacacagacttacatttgt aacgtgaatcacaagcctag caacaccaaggtcgacaaga gagttgaaccaaagagttgt gattgccactgtcctccctg cccagctcctgagctgcttg gcggtcccagtgtcttcttg tttccccctaaacccaaaga caccctgatgatctcaagga ctcccgaggtgacatgcgtg gtggtggatgtgtctcatga ggacccagaggtgaagttca actggtacgtggacggcgtg gaggtgcacaacgccaagac caagcccagagaggagcagt acaacagcacctacagggtg gtgtccgtgctgaccgtgct gcaccaggactggctgaacg gcaaggagtacaagtgtaag gtgtccaacaaggccctgcc agccccaatcgaaaagacca tcagcaaggccaagggccag ccaagagagccccaggtgta caccctgccaccccagcaggg aggagatgaccaagaaccag gtgtccctgacctgtctggt gaagggcttctacccaagcg acatcgccgtggagtgggag agcaacggccagcccgagaa caactacaagaccaccccc cagtgctggacagcgacggc agcttcttcctgtacagcaa gctgaccgtggacaagagca gatggcagcagggcaacgtg ttcagctgctccgtgatgca cgaggccctgcacaaccact acacccagaagagcctgagc ctgtccccaggctga |
| 22 | DNA encoding AbA CDR-H1 | ggctacatcttcacagcata cacc |
| 23 | DNA encoding AbA CDR-H2 | attaaacccaacaatgggct ggcc |
| 24 | DNA encoding AbA CDR-H3 | gccaggagcgaaattacaac agaattcgattac |
| 25 | DNA encoding AbA Light Chain | atggaaactgatacactgct gctgtgggtcctgctgctgt gggtccctggaagcacaggg gacattgtgatgacccagtc tcccgatagcctggccgtgt ccctgggcgagagggctacc atcaactgtaaaagctccga atctgtggactcttacgcaa acagctttctgcactggtat cagcaaaagccaggccaacc tccaaagctgctgatttaca gggcttctaccaggagagc ggcgtgcccgataggttcag cggatctggcagcggcaccg actttacactgaccatctcc agcctgcaggccgaagatgt ggcagtctattactgccagc agtccaaggaggacccctg actttcgggggtggtactaa agtggagatcaagcgtacgg tggccgctcccagcgtgttc atcttcccccaagcgacga gcagctgaagagcggcaccg ccagcgtggtgtgtctgctg aacaacttctaccccaggga ggccaaggtgcagtggaagg tggacaacgccctgcagagc ggcaacagccaggagagcgt caccgagcaggacagcaagg actccacctacagcctgagc agcaccctgaccctgagcaa ggccgactacgagaagcaca aggtgtacgcctgtgaggtg acccaccagggcctgtccag ccccg tgaccaagagcttcaacagg ggcgagtgctga |
| 26 | DNA encoding AbA CDR-L1 | gaatctgtggactcttacgc aaacagcttt |
| 27 | DNA encoding AbA CDR-L2 | agggcttct |
| 28 | DNA encoding AbA CDR-L3 | cagcagtccaaggaggaccc cctgact |

What is claimed:

1. An anti-c-Met antibody drug conjugate comprising the following structure:

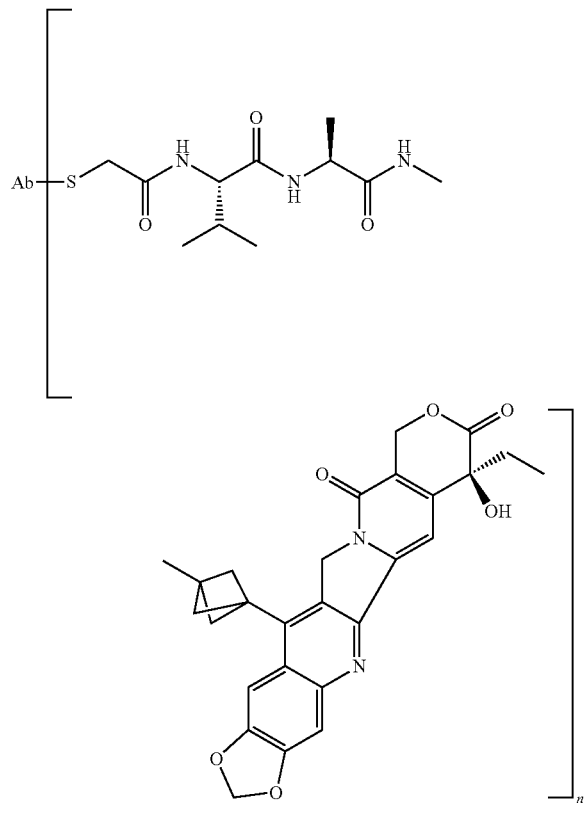

wherein n is an integer from 1 to 10, and wherein Ab is an $IgG_1$ anti-c-Met antibody comprising
a heavy chain variable region comprising a heavy chain CDR3 domain comprising the amino acid sequence shown as SEQ ID NO: 3, a heavy chain CDR2 domain comprising the amino acid sequence shown as SEQ ID NO: 2, and a heavy chain CDR1 domain comprising the amino acid sequence shown as SEQ ID NO: 1; and
a light chain variable region comprising a light chain CDR3 domain comprising the amino acid sequence shown as SEQ ID NO: 6, a light chain CDR2 domain comprising the amino acid sequence shown as SEQ ID NO: 5, and a light chain CDR1 domain comprising the amino acid sequence shown as SEQ ID NO: 4.

2. The anti-c-Met antibody drug conjugate according claim 1, wherein the antibody Ab comprises a heavy chain variable region comprising the amino acid sequence set forth as SEQ ID NO: 7 and a light chain variable region comprising the amino acid sequence set forth as SEQ ID NO: 8.

3. The anti-c-Met antibody drug conjugate according to claim 1, wherein the antibody Ab comprises a heavy chain comprising the amino acid sequence set forth as SEQ ID NO: 9 and a light chain comprising the amino acid sequence set forth as SEQ ID NO: 10.

4. The anti-c-Met antibody drug conjugate according to claim 3, wherein n is 6.

5. The anti-c-Met antibody drug conjugate according to claim 3, wherein n is 2.

6. The anti-c-Met antibody drug conjugate according to claim 3, wherein n is 4.

7. The anti-c-Met antibody drug conjugate according to claim 3, wherein n is 8.

8. The anti-c-Met antibody drug conjugate according to claim 3, wherein n is 10.

* * * * *

UNITED STATES PATENT AND TRADEMARK OFFICE
CERTIFICATE OF CORRECTION

| | | |
|---|---|---|
| PATENT NO. | : 11,633,497 B2 | Page 1 of 1 |
| APPLICATION NO. | : 17/661450 | |
| DATED | : April 25, 2023 | |
| INVENTOR(S) | : Andrew C. Phillips et al. | |

It is certified that error appears in the above-identified patent and that said Letters Patent is hereby corrected as shown below:

In the Claims

Column 55, Claim number 1, the structure is as follows:

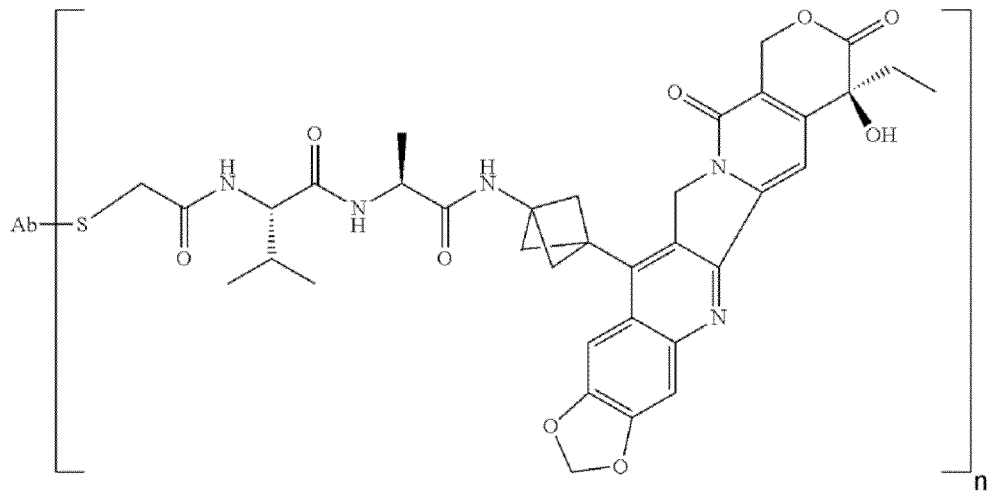

Signed and Sealed this
Fifteenth Day of April, 2025

Coke Morgan Stewart
*Acting Director of the United States Patent and Trademark Office*

SEQUENCE LISTING

<160> NUMBER OF SEQ ID NOS: 28

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 1

```
Gly Tyr Ile Phe Thr Ala Tyr Thr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 2

Ile Lys Pro Asn Asn Gly Leu Ala
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 3

Ala Arg Ser Glu Ile Thr Thr Glu Phe Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 4

Glu Ser Val Asp Ser Tyr Ala Asn Ser Phe
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 5

Arg Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Gln Gln Ser Lys Glu Asp Pro Leu Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 7

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Ile Phe Thr Ala Tyr
                20                  25                  30

Thr Met His Trp Val Arg Gln Ala Pro Gly Gln Gly Leu Glu Trp Met
            35                  40                  45

Gly Trp Ile Lys Pro Asn Asn Gly Leu Ala Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Ser Glu Ile Thr Thr Glu Phe Asp Tyr Trp Gly Gln Gly Thr
                100                 105                 110

Leu Val Thr Val Ser Ser
            115

<210> SEQ ID NO 8
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
                20                  25                  30

Ala Asn Ser Phe Leu His Trp Tyr Gln Gln Lys Pro Gly Gln Pro Pro
            35                  40                  45

Lys Leu Leu Ile Tyr Arg Ala Ser Thr Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys
                100                 105                 110

<210> SEQ ID NO 9
<211> LENGTH: 445
<212> TYPE: PRT
<213> ORGANISM: Artificial Sequence
<220> FEATURE:
<223> OTHER INFORMATION: Synthetic polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
                20                  25                  30

Thr Met His Trp Val Arg Gln Ala Pro Gly Gln Gly Leu Glu Trp Met
            35                  40                  45

Gly Trp Ile Lys Pro Asn Asn Gly Leu Ala Asn Tyr Ala Gln Lys Phe
        50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                 85                  90                  95

Ala Arg Ser Glu Ile Thr Thr Glu Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Cys His
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 10
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 10
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Leu His Trp Tyr Gln Gln Lys Pro Gly Gln Pro Pro
            35                  40                  45

Lys Leu Leu Ile Tyr Arg Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
            85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 11
<211> LENGTH: 460
<212> TYPE: PRT
<213> ORGANISM: Artificial Sequence
<220> FEATURE:
<223> OTHER INFORMATION: Synthetic polypeptide

<400> SEQUENCE: 11

Glu Glu Gln Val Leu Glu Ser Gly Gly Gly Leu Val Lys Pro Gly Gly
1               5                   10                  15

Ser Leu Arg Leu Ser Cys Ala Ala Ser Gly Phe Thr Phe Ser Pro Tyr
            20                  25                  30

Ser Val Phe Trp Val Arg Gln Ala Pro Gly Lys Gly Leu Glu Trp Val
            35                  40                  45

Ser Ser Ile Asn Ser Asp Ser Thr Tyr Lys Tyr Ala Asp Ser Val
50                  55                  60

Lys Gly Arg Phe Thr Ile Ser Arg Asp Asn Ala Glu Asn Ser Ile Phe
65                  70                  75                  80

Leu Gln Met Asn Ser Leu Arg Ala Glu Asp Thr Ala Val Tyr Tyr Cys
            85                  90                  95

Ala Arg Asp Arg Ser Tyr Tyr Ala Phe Ser Gly Ser Leu Ser Asp
            100                 105                 110

Tyr Tyr Tyr Gly Leu Asp Val Trp Gly Gln Gly Thr Thr Val Ile Val
            115                 120                 125

Ser Ser Ala Ser Thr Lys Gly Pro Ser Val Phe Pro Leu Ala Pro Ser
            130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
            165                 170                 175

Thr Ser Gly Val His Thr Phe Pro Ala Val Leu Gln Ser Ser Gly Leu
        180                 185                 190

Tyr Ser Leu Ser Ser Val Val Thr Val Pro Ser Ser Ser Leu Gly Thr
    195                 200                 205

Gln Thr Tyr Ile Cys Asn Val Asn His Lys Pro Ser Asn Thr Lys Val
210                 215                 220

Asp Lys Lys Val Glu Pro Lys Ser Cys Asp Lys Thr His Thr Cys Pro
225                 230                 235                 240

Pro Cys Pro Ala Pro Glu Ala Ala Gly Gly Pro Ser Val Phe Leu Phe
            245                 250                 255

Pro Pro Lys Pro Lys Asp Thr Leu Met Ile Ser Arg Thr Pro Glu Val
        260                 265                 270

Thr Cys Val Val Val Asp Val Ser His Glu Asp Pro Glu Val Lys Phe
    275                 280                 285

Asn Trp Tyr Val Asp Gly Val Glu Val His Asn Ala Lys Thr Lys Pro
290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
            325                 330                 335

Ser Asn Lys Ala Leu Pro Ala Pro Ile Glu Lys Thr Ile Ser Lys Ala
        340                 345                 350

Lys Gly Gln Pro Arg Glu Pro Gln Val Tyr Thr Leu Pro Pro Ser Arg
    355                 360                 365

Asp Glu Leu Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
            405                 410                 415

Phe Phe Leu Tyr Ser Lys Leu Thr Val Asp Lys Ser Arg Trp Gln Gln
        420                 425                 430

Gly Asn Val Phe Ser Cys Ser Val Met His Glu Ala Leu His Asn His
    435                 440                 445

Tyr Thr Gln Lys Ser Leu Ser Leu Ser Pro Gly Lys
450                 455                 460

<210> SEQ ID NO 12
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 12

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Val Gln Lys Pro Gly Gln Ser
        35                  40                  45

```
Pro Gln Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Lys Ile
 65              70                  75                      80

Ser Arg Val Glu Thr Glu Asp Val Gly Val Tyr Tyr Cys Met Gln Ala
                 85                  90                  95

Leu Gln Ile Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Ala
    210                 215
```

<210> SEQ ID NO 13
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 13

```
Glu Val Gln Leu Gln Gln Ser Gly Pro Glu Leu Val Lys Pro Gly Ala
 1               5                  10                  15

Ser Val Lys Ile Ser Cys Lys Thr Ser Gly Tyr Ile Phe Thr Ala Tyr
                20                  25                  30

Thr Met His Trp Val Arg Gln Ser Leu Gly Glu Ser Leu Asp Trp Ile
            35                  40                  45

Gly Gly Ile Lys Pro Asn Asn Gly Leu Ala Asn Tyr Asn Gln Lys Phe
        50                  55                  60

Lys Gly Lys Ala Thr Leu Thr Val Asp Lys Ser Ser Ser Thr Ala Tyr
 65                  70                  75                  80

Met Asp Leu Arg Ser Leu Thr Ser Glu Asp Ser Ala Val Tyr Tyr Cys
                 85                  90                  95

Ala Arg Ser Glu Ile Thr Thr Glu Phe Asp Tyr Trp Gly Gln Gly Thr
                100                 105                 110

Ala Leu Thr Val Ser Ser
        115
```

<210> SEQ ID NO 14
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 14

```
Asp Ile Val Leu Thr Gln Ser Pro Ala Ser Leu Ala Val Ser Leu Gly
 1               5                  10                  15
```

```
Gln Arg Ala Thr Ile Ser Cys Arg Ala Ser Glu Ser Val Asp Ser Tyr
                20                  25                  30

Ala Asn Ser Phe Met His Trp Tyr Gln Gln Lys Pro Gly Gln Pro Pro
             35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Lys
                 85                  90                  95

Glu Asp Pro Leu Thr Phe Gly Ser Gly Thr Lys Leu Glu Met Lys
            100                 105                 110

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 15

Gly Tyr Ile Phe Thr Ala Tyr Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 16

Ile Lys Pro Asn Asn Gly Leu Ala
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 17

Ala Arg Ser Glu Ile Thr Thr Glu Phe Asp Tyr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 18

Glu Ser Val Asp Ser Tyr Ala Asn Ser Phe
1               5                   10

<210> SEQ ID NO 19
<211> LENGTH: 3
<212> TYPE: PRT
<213> ORGANISM: Artificial Sequence
<220> FEATURE:
<223> OTHER INFORMATION: Synthetic polypeptide
```

<400> SEQUENCE: 19

Arg Ala Ser
1

<210> SEQ ID NO 20
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 20

Gln Gln Ser Lys Glu Asp Pro Leu Thr
1               5

<210> SEQ ID NO 21
<211> LENGTH: 1395
<212> TYPE: DNA
<213> ORGANISM: Artificial Sequence
<220> FEATURE:
<223> OTHER INFORMATION: Synthetic polynucleotide

<400> SEQUENCE: 21

```
atgggatggt cttggatctt tctgctgttt ctgtctggta ctgctggtgt gctgagccag      60
gtccagctgg tgcaatccgg cgcagaggtg aagaagccag cgcttccgt gaaggtgagc     120
tgtaaggcct ctggctacat cttcacagca tacaccatgc actgggtgag caagctcct    180
gggcagggac tggagtggat gggatggatt aaacccaaca tgggctggc caactacgcc    240
cagaaattcc agggtagggt cactatgaca agggatacca gcatcagcac cgcatatatg    300
gagctgagca ggctgaggtc tgacgacact gctgtctatt attgcgccag gagcgaaatt    360
acaacagaat tcgattactg ggggcagggc accctggtga ccgtgtcctc tgccagcacc    420
aagggcccaa gcgtgttccc cctggccccc agcagcaaga gcaccagcgg cggcacagcc    480
gccctgggct gcctggtgaa ggactacttc cccgagcccg tgaccgtgtc ctggaacagc    540
ggagccctca cttctggagt tcataccttc ccagcagtat gcagagcag tggcctgtat    600
tcactgtctt ccgtcgtaac agttccatcc tccagcctcg ggacacagac ttacatttgt    660
aacgtgaatc acaagcctag caacaccaag gtcgacaaga gagttgaacc aaagagttgt    720
gattgccact gtcctccctg cccagctcct gagctgcttg gcggtcccag tgtcttcttg    780
tttccccta acccaaaga caccctgatg atctcaagga ctcccgaggt gacatgcgtg    840
gtggtggatg tgtctcatga ggacccgag gtgaagttca actggtacgt ggacggcgtg    900
gaggtgcaca acgccaagac caagcccaga gaggagcagt acaacagcac ctacagggtg    960
gtgtccgtgc tgaccgtgct gcaccaggac tggctgaacg gcaaggagta caagtgtaag   1020
gtgtccaaca aggccctgcc agccccaatc gaaaagacca tcagcaaggc caagggccag   1080
ccaagagagc cccaggtgta caccctgcca cccagcaggg aggagatgac caagaaccag   1140
gtgtccctga cctgtctggt gaagggcttc tacccaagcg acatcgccgt ggagtgggag   1200
agcaacggcc agcccgagaa caactacaag accaccccccc cagtgctgga cagcgacggc   1260
agcttcttcc tgtacagcaa gctgaccgtg gacaagagca atggcagca gggcaacgtg   1320
ttcagctgct ccgtgatgca cgaggccctg cacaaccact acacccagaa gagcctgagc   1380
ctgtccccag gctga                                                    1395
```

<210> SEQ ID NO 22
<211> LENGTH: 24

```
<212> TYPE: DNA
<213> ORGANISM: Artificial Sequence
<220> FEATURE:
<223> OTHER INFORMATION: Synthetic polynucleotide

<400> SEQUENCE: 22
ggctacatct tcacagcata cacc                                          24

<210> SEQ ID NO 23
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 23
attaaaccca acaatgggct ggcc                                          24

<210> SEQ ID NO 24
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 24
gccaggagcg aaattacaac agaattcgat tac                                33

<210> SEQ ID NO 25
<211> LENGTH: 717
<212> TYPE: DNA
<213> ORGANISM: Artificial Sequence
<220> FEATURE:
<223> OTHER INFORMATION: Synthetic polynucleotide

<400> SEQUENCE: 25
atggaaactg atacactgct gctgtgggtc ctgctgctgt gggtccctgg aagcacaggg    60
gacattgtga tgacccagtc tcccgatagc ctggccgtgt ccctgggcga gagggctacc   120
atcaactgta aaagctccga atctgtggac tcttacgcaa acagctttct gcactggtat   180
cagcaaaagc caggccaacc tccaaagctg ctgatttaca gggcttctac cagggagagc   240
ggcgtgcccg ataggttcag cggatctggc agcggcaccg actttacact gaccatctcc   300
agcctgcagg ccgaagatgt ggcagtctat tactgccagc agtccaagga ggacccctg    360 actttcgggg gtggtactaa agtggagatc aagcgtacgg tggccgctcc cagcgtgttc   420
atcttccccc caagcgacga gcagctgaag agcggcaccg ccagcgtggt gtgtctgctg   480
aacaacttct accccaggga ggccaaggtg cagtggaagg tggacaacgc cctgcagagc   540
ggcaacagcc aggagagcgt caccgagcag gacagcaagg actccaccta cagcctgagc   600
agcaccctga ccctgagcaa ggccgactac gagaagcaca aggtgtacgc ctgtgaggtg   660
acccaccagg gcctgtccag ccccgtgacc aagagcttca caggggcga gtgctga      717

<210> SEQ ID NO 26
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 26
gaatctgtgg actcttacgc aaacagcttt                                    30
```

```
<210> SEQ ID NO 27
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 27 agggcttct                                                                 9

<210> SEQ ID NO 28
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 28
cagcagtcca aggaggaccc cctgact                                             27
```